United States Patent [19]
Manome et al.

[11] Patent Number: 6,009,755
[45] Date of Patent: Jan. 4, 2000

[54] ULTRASONIC TRANSCEIVER DISPLAYING MODIFIED B SCOPE

[75] Inventors: Yuuichi Manome; Mitsuhiro Koike; Shusou Wadaka; Tomonori Kimura; Shumpei Kameyama, all of Tokyo, Japan

[73] Assignee: Mitsubishi Denki Kabushiki Kaisha, Tokyo, Japan

[21] Appl. No.: 08/965,193

[22] Filed: Nov. 6, 1997

[30] Foreign Application Priority Data

Nov. 8, 1996 [JP] Japan .................... 8-296659

[51] Int. Cl.$^7$ .................... G01N 29/06; G01N 29/10
[52] U.S. Cl. .................... 73/602; 73/626; 73/628; 73/629
[58] Field of Search .................... 73/602, 597, 598, 73/599, 600, 618, 620, 622, 625, 626, 627, 628, 629, 641, 633

[56] References Cited

U.S. PATENT DOCUMENTS

| | | | |
|---|---|---|---|
| 4,431,007 | 2/1984 | Amazeen et al. | 73/626 |
| 4,604,697 | 8/1986 | Luthra et al. | 73/602 |
| 4,841,489 | 6/1989 | Ozaki et al. | 73/633 |
| 5,042,305 | 8/1991 | Takishita | 73/625 |
| 5,245,587 | 9/1993 | Hutson | 367/100 |

FOREIGN PATENT DOCUMENTS

| | | |
|---|---|---|
| 4-9656 | 2/1992 | Japan . |
| 4-289453 | 10/1992 | Japan . |
| 7-9657 | 2/1995 | Japan . |
| 7-81992 | 9/1995 | Japan . |
| 7-81993 | 9/1995 | Japan . |
| 7-81994 | 9/1995 | Japan . |
| 7-81995 | 9/1995 | Japan . |
| 7-85076 | 9/1995 | Japan . |
| 7-85077 | 9/1995 | Japan . |

OTHER PUBLICATIONS

Toshio Fujiyoshi, "DGS diagram of angle probe," New Handbook of Non–Destructive Inspection, NDC 501.55, The Japanese Society for Non–Destructive Inspection, The Nikkan Kogyo Shinbun Ltd., Oct. 15, 1992, First Edition, First Printing; Published. (English language translation, pp. 1–3 attached).

Kenji Okubo, "4.2 Angle Beam Technique," Ultrasonic Testing (New revised edition), NDC 501.55, Japan Society for the Promotion of Science, 19$^{th}$ committee on Steel Making, The Nikkan Kogyo Shinbun Ltd., Jul. 30, 1974 New revised edition; Published; Jun. 1, 1984 New revised edition, Sicth printing, Published. (English language translation, pp. 1–7 attached).

*Primary Examiner*—Hezron Williams
*Assistant Examiner*—Rose M. Miller
*Attorney, Agent, or Firm*—Burns, Doane, Swecker & Mathis, LLP

[57] ABSTRACT

An ultrasonic transceiver has a function of displaying a modified B scope. The ultrasonic transceiver transmits ultrasonics to an inner part of a test object at an angle of inclination to a surface of the test object, receives echoes from discontinuity in the test object, and displays, based on an outcome of the reception, an image which shows a state of transmission of the ultrasonics in the test object. When displaying the image, origins of time axes on the screen are shifted through a coordinate transformation of the outcome of reception to avoid the difference in lateral positions of images of single discontinuity. Consequently, it is possible to accurately discern the location, size, configuration, and posture of the discontinuity when the outcome of reception is displayed in a rectangular display window.

21 Claims, 32 Drawing Sheets

ULTRASONIC TRANSCEIVER DISPLAYING MODIFIED B SCOPE

BACKGROUND OF THE INVENTION

1. Field of the Invention

The present invention relates to a device for searching and examining the inside of a test object by moving a probe along the surface of the test object without causing damage to the object in order to determine the existence and nature of any discontinuities.

2. Description of the Related Art

An ultrasonic transceiver is a device which enables searching the internal condition of a test object without damaging the object. The ultrasonic transceiver transmits ultrasonics into the test is object, receives reflections from the inside of the object, and then converts an outcome of the reception into a visual image. The visual image, which can be provided by the ultrasonic transceiver, may be, for example, an "UA scope", a "B scope", etc.

In the A scope, the transmission length of an ultrasonic inside the test object, namely, a time period elapsed immediately after commencement of the transmission is designated as an axis of abscissa, and power or amplitude of an ultrasonic received from the inside of the test object is designated as an axis of ordinate. The A scope can be obtained in such a manner that an ultrasonic probe, which is fixed on a discretionary location of the surface of the test object, transmits ultrasonics into the test object, then receives the ultrasonics from the inside of the test object, and video signals are generated basing on reception outputs of the ultrasonic probe. The A scope has an advantage of enabling users to directly see how deep the discontinuity, which differs from the other interior parts of the test object in the transmission characteristics of ultrasonics, exists in the test object.

In the B scope, the transmission length of an ultrasonic in the test object, namely, a time period elapsed immediately after commencement of the transmission is designated as an axis of abscissa, and a direction of the movement of a probe is designated as an axis of ordinate. The B scope can be obtained in such a manner that a discretionary cross section of the test object is scanned by ultrasonics which are repeatedly transmitted and received, and video signals are generated basing on a reception output of the ultrasonic probe. The transmission and the reception of ultrasonics are carried out at a certain position of the surface of the test object or carried out shifting the position of the transmission along the surface of the test object. The B scope has an advantage of enabling users to directly judge at which location of the test object the discontinuity exists by viewing the cross section of the test object scanned by ultrasonics transmitted from the ultrasonic probe. The B scope is often used with display enhancement in which an intense reception output is displayed by an image with a large area or a color of display is changed according to strength of the reception output.

The ultrasonic transceiver is classified into two types: one is a type using an ultrasonic probe from which ultrasonics are transmitted to a direction perpendicular to the surface of the test object; the other is a type which ultrasonics are transmitted in a nonperpendicular direction. Although either type can provide both the A scope and the B scope, with the nonperpendicular type, the B scope provided is not useful. This is because an inclination of the direction of the transmission causes a cross section scanned by ultrasonics to be parallelogrammic, but generally a display window to be used for displaying the B scope is rectangular, as shown in FIG. 39. In other words, even though the B scope is formed, it is difficult to accurately discern the location, configuration, posture, and such characteristics of the discontinuity from the image.

SUMMARY OF THE INVENTION

One of the objects of the present invention is to provide a useful B scope from which the discontinuity of an object can easily be observed even when a type of ultrasonic transceiver using an ultrasonic probe from which ultrasonics are transmitted out of perpendicular to the surface of a test object is used. For such a purpose, in the present invention, a modified B scope, namely, a scope obtained through processing according to a method which is novel and different from a method to obtain a conventional B scope, on the reception output.

The present invention may be embodied as a signal processor, as an ultrasonic transceiver using the signal processor, or as an ultrasonic flaw detector which is one application of the ultrasonic transceiver. The ultrasonic transceiver transmits ultrasonics into a test object and receives an echo from the interior of the test object, while shifting a ultrasonic transmitting position along the surface of the test object and maintaining an ultrasonic transmitting direction inclined with respect to the surface of the test object. The ultrasonic transceiver displays an image indicative of presence or nature of a discontinuity in the test object on the screen of a display device based on the reception results. When the ultrasonic transceiver is implemented as an ultrasonic flaw detector for searching for discontinuity in the test object damaging the test object, which may be, for example, in the form of a board material, a tubular material, or a welded workpiece, images indicative of the discontinuity such as a foreign contaminant, an aperture, or a structural defect in the test object are displayed on the screen. So-called immersion technique or local immersion technique in which the observation is carried out through filmy water on the surface of the test object can be used in this ultrasonic flaw detector.

The signal processor according to the present invention modifies the result of the reception so that images obtained by modifying the result of the reception are displayed on the screen. One of the characteristic features of the present invention lies in the processing performed by the signal processor to obtain the modified images, while another characteristic feature lies in the modified images, in other words, in the modified B scope. The modified B scope has two modes, one mode is a time origin shifting mode modifying the received output of an angle type ultrasonic prove so that images of discontinuities in the test object with the same ultrasonic transmission time (same elapsed time from the incidence of ultrasonics into the test object to the reception of echoes from the discontinuities) are displayed at positions on a line parallel to a scanning direction axis, while the second mode is a time axis inclining mode modifying the received output so that the cross-section of the test object is displayed with no inclination with respect to the screen.

In the time origin shifting mode, the signal processor modifies the result of reception on the basis of the ultrasonic transmitting position and an angle information indicative of the ultrasonic transmitting direction, to shift the origin position of the time axis as the ultrasonic transmitting position shifts. Further, the screen of the display device has at least two axes, a time axis representing a time elapse from ultrasonic incidence into the test object and a scanning direction axis representing a shifting direction of the ultrasonic transmitting position. By shifting the origin position according to the shift of the ultrasonic transmitting position, a plurality of images with the same ultrasonic transmission time are displayed on a line parallel to the scanning direction axis on the screen.

In the time axis inclining mode, the signal processor modifies the result of reception on the basis of the ultrasonic transmitting position and the angle information indicative of ultrasonic transmitting direction, so that the time axis is inclined with respect to the scanning direction axis and a depth axis on the screen to display the cross-section of the test object with no inclination. The scanning direction axis and the depth axis in this mode represent positions along and perpendicular to the shifting direction of the ultrasonic transmitting direction, respectively.

In the present invention, therefore, the distortion of the displayed images are avoided or prevented. For instance, in the time origin shifting mode, a plurality of echoes from same discontinuity obtained at mutually different ultrasonic transmitting positions are displayed at points having a same distance from the line on which the corresponding time origins are aligned. In the time axis inclining mode, the cross-section of the test object is displayed on the screen without inclination. More specifically, if the display window has a rectangular shape, the echoes from the rectangular area in the test object are displayed without distortion and thus the user can discern the nature of the discontinuity more accurately in this mode. Note that the present invention is not limited to rectangular display rs windows and thus display windows having other shapes and full screen displays are also available. Further, it is possible to combine the time origin shifting mode and the time axis inclining mode.

Further, in the time origin shifting mode or its combination to the time axis inclining mode, since the angle information indicative of the ultrasonic transmitting direction is utilized to modify the images, it is possible to avoid the influence of unnecessary waves. Specifically speaking, the difference in the transmission mode causes the difference in transmission velocity etc. If the transducer receives ultrasonics including a plurality of components which correspond to mutually different transmission modes and supplies them to the display device as they are, mutually overlapped images indicative of respective modes are displayed, and thus the observation of discontinuity in the test object is interrupted. In actuality, the difference in transmission modes causes not only a difference in the transmission velocity but also a difference in the refraction angle at the surface of the test object. In the present invention, to avoid interruption of observation, the signal processor selectively enhances images obtained through the desirable transmission mode by time origin shifting processing utilizing the angle information. Therefore, even when a main beam width of an ultrasonic transducer in the angle type ultrasonic probe is not narrow enough, the unnecessary waves such as a wave whose transmission mode differs from that of the wave to be observed are avoided from the images based on the processed received output of the transducer. Further, the selection of transmission mode for observing through the processing based on the angle information enables indirect wave observation and the mode-converted wave observation.

In one embodiment of the present invention, a single angle type ultrasonic probe is provided with a scanning mechanism to realize a mechanical scanning system. The angle type ultrasonic probe is arranged on the surface of the test object, transmits ultrasonics into the test object along a direction which is inclined with respect to the surface of the test object, and receives ultrasonics i.e. echoes from a discontinuity in the test object. The scanning mechanism is a mechanism for shifting the ultrasonic transmitting position along the surface of the test object while maintaining the inclined ultrasonic transmitting direction. The ultrasonic transmitting position and direction are defined as the position from which the angle type ultrasonic probe transmits ultrasonics into the test object and the shifting direction of the position, respectively. To reflect the effect of the refraction of the ultrasonics at the surface, the ultrasonic transmitting position is defined as an apparent position of the transducer.

In another embodiment of the present invention, a plurality of angle type ultrasonic probes are provided with a switch circuit to realize an electronic scanning system. The angle type ultrasonic probes, arranged along a line parallel to the surface of the test object and provided with its ultrasonic transmitting direction inclined with respect to the surface of the test object, transmits ultrasonics to and receives ultrasonics from the interior of the test object. The switch circuit selectively and sequentially operates the plurality of angle type ultrasonic probes along the liner so that the ultrasonic transmitting position shifts along the surface of the test object while maintaining the ultrasonic transmitting direction inclined with respect to the surface. The plurality of angle type ultrasonic probes may implemented as a probe array consisting of a single ceramic body on which a plurality of ultrasonic transducers are fixed with a predetermined angle. Alternatively, the plurality of angle type ultrasonic probes may implemented as an array of individual angle type ultrasonic probes held by a single holder having a plurality of rooms or chambers in which individual probes are positioned.

In preferable embodiments of the present invention, a position detector is provided to detect the ultrasonic transmitting position. The detected position can be utilized in the signal processor, along with angle information indicative of the ultrasonic transmitting direction, to derive the shift width of the origin position of the time axis in the time origin shifting mode, for instance. The time origin shifting, the time axis inclining and the combination thereof may be realized by utilizing a memory in which the processed received output are stored to supply the processed received output to the display device and by modifying a write address to the memory in compliance with the shift width. Further, by providing a controller which supplies the angle information indicative of the ultrasonic transmitting direction in response to user input, the adjustment of the display imagesandthe selection of the ultrasonic mode to be displayed are enabled.

In the present invention, the shifting of the ultrasonic transmitting position is not limited to a linear movement. Although the main beam will scan a curved surface or volume in the test object when the movement is non-linear, it is possible to neglect the curve of the scanned portion if the observation period is short enough.

The image format to be used on the screen may be controlled by the controller which instructs, to the signal processor, which one of first to third images should be displayed. The first image is a format in which the image having a large area indicates strong echo, the second image is a format in which each image has a color indicative of signal strength of the echo, and the third image is a format in which the image indicates a signal waveform of the received output. The third image enables observation of the phase and the variation of the echo and therefore the detailed observation of a state of reflections and the nature of the discontinuity.

In the preferred embodiments of the present invention, additional processing on the received output or processed received output is carried out. For example, an aperture synthesizer performing an aperture synthesis on the received output or the processed received output to be supplied to the display device may be provided. The aperture synthesizer apparently enhances the aperture of the angle type ultrasonic probe and thus improves the bearing resolution and the signal-to-noise ratio, by combining the received output or the processed received output to a previously-obtained received output or a processed received output. When a table correlating the ultrasonic transmitting position, a distance from the ultrasonic transmitting position and a position in the test object is provided, the processing speed of the aperture synthesizer is improved since complex calculation of aperture synthesis is replaced with the simpler process of referring to a table.

Further, a deconvolution filter which performs a deconvolution on the received output or the processed received output to be supplied to the display device may be provided. The deconvolution is a process for improving the time resolution and range resolution, by convoluting characteristics of the received output or the processed received output and characteristics which is reciprocal to characteristics relating to transmitting and receiving operation of ultrasonics and is included in the characteristics of the received output. Additionally, a pulse compression filter performing a pulse compression on the received output or the processed received output to be supplied to the display device may be provided. Pulse compression is a process for increasing an energy density in the received output and for improving the signal-to-noise ratio, by utilizing existing correlation between a phase modulation signal, previously utilized to modulate transmitting ultrasonics, and the received output. Finally, the combination or the switching operation of the deconvolution filter and the pulse compression filter can be realized by utilizing a characteristic switching type filter such as a finite impulse response filter that operates, in response to an instruction from the controller, as the deconvolution filter, the pulse compression filter, or a combination filter having characteristics which are equivalent to a combination of the deconvolution filter and the pulse compression filter.

In preferred embodiments of the present invention, a display processor for controlling an arrangement of a plurality of display windows on a screen of the display device is provided. The display windows are classified into the following types: a detection result display window for displaying an image indicative of the processed received output; a gate inside window for displaying an image which is an extracted part of the image obtained from the processed received output or for displaying a modified image obtained by modifying the extracted part; and a parameter display window for displaying a condition which is manually set by a user or automatically set by the ultrasonic transceiver.

A plurality of detection result display windows may be provided to display mutually different images each indicative of the processed received output. For example, images showing a same processed received output in mutually different image formats are displayed on the windows. In another case, images showing mutually different processed received outputs obtained by performing mutually different type of processes on a same received output are displayed. Furthermore, images showing mutually different processed received outputs each obtained from different test objects may be displayed. By displaying a plurality of images side-by-side so that the user can compare them, more detailed observation becomes possible.

A gate inside window is utilized to cut out a designated part of the image on the detection result display window in response to the user input. The user can extract a part of the processed received output as the aforementioned extracted part to be displayed on a gate inside window by designating an area on the time axis on the screen with a time. axis gate marker, by designating an area on the scanning direction axis with a scanning direction axis gate marker, or by designating one ultrasonic transmitting position and an area on the time axis with a probe position marker and the time axis gate marker. A parameter display window is utilized to display a condition concerning the transmittance of ultrasonics, the reception of ultrasonics or the display of the processed received output.

A preferred embodiment of the present invention will be subsequently described with reference to the attached drawings. For explanatory reasons, many block diagrams are used, but this embodiment is applicable to software.

DESCRIPTION OF THE PREFERRED EMBODIMENTS

SYSTEM COMPOSITION

Figure 1:
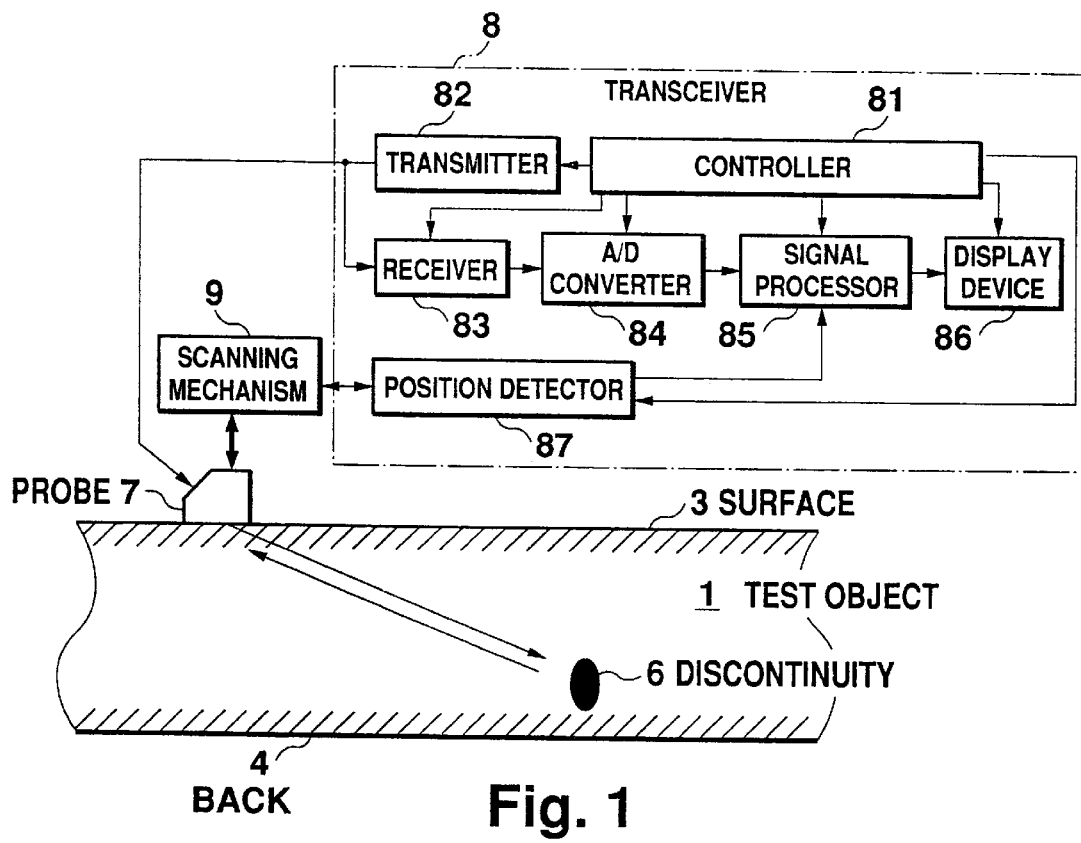
FIG. 1 is a block diagram showing the fundamental arrangement of each embodiment of the present invention.

FIG. 1 shows system composition which is common to respective embodiments to be explained hereinafter. This is a system which obtains, through use of ultrasonics, data as to whether or not discontinuity 6 exists in a test object 1 and the location, size, configuration, and posture of the discontinuity 6. When this sort of system is applied to various industrial products such as plates and tubing, and welded articles, the system is called an ultrasonic flaw detector and is utilized to detect discontinuity such as foreign contaminants mixed, cracks arising, or the like in a product. As the foreign contaminants and the crack, a slug or a peripheral medium which may enter into a product through a weld zone and a crack of a root running part, a crater crack of a welding end, incomplete fusion of a weld zone, poor penetration of a weld zone, a blowhole, a wormhole, a hot crack, or the like are known. The ultrasonic flaw detector is suitable for inspecting products without damaging them, for example, during an inspection process or a quality assessment process, each of which is carried out after a production process, or a re-examination process for products which are made a claim as defective commodities at a market. In the explanation which will be given hereunder, application to the ultrasonic flaw detection is premised on in order to provide a specific description. However, it is noted that the present invention covers other application, for example an ultrasonic diagnosis of a living body.

Figure 2:
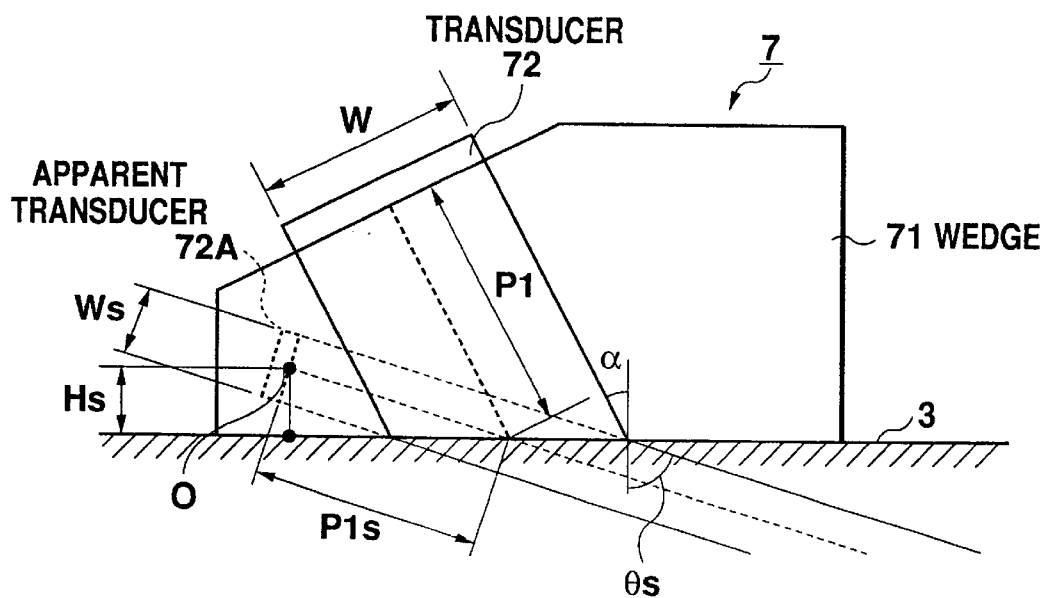
FIG. 2 is a conceptual drawing which shows the structure of a probe and a refraction of ultrasonics on the surface of a test object.

There are two types of ultrasonic flaw detection; the so-called normal beam and angle beam techniques. In the normal beam technique, ultrasonics are transmitted into the test object 1 so that they travel in a direction perpendicular to the surface 3 of the test object 1. On the other hand, in the angle beam technique, ultrasonics are transmitted into the test object 1 so that they travel in a direction which is out of the perpendicular to the surface 3 of the test object 1. The system shown in FIG. 1 is a system for the angle beam technique. More specifically, a probe 7 in contact with the surface 3 of the test object transmits ultrasonics in a direction which is out of the perpendicular to the surface 3 and receives the ultrasonics which return from the inside of the test object 1. To be more precise, the probe 7 consists of a wedge 71 and a transducer 72 as shown in FIG. 2. The wedge 71 is made of raw material, such as acrylic, and has a diagonally cut portion on which the transducer 72 such as a piezoelectric ceramics transducer having a circular shape is fixed. Although FIG. 2 is drawn as if the under surface of edge 71 were directly in contact with the surface 3 of the test object, the edge is not in fact always directly in contact with the surface 3. For example, when a method called as a immersion technique or a local immersion technique is applied, water intervenes between the undersurface of the wedge 71 and the surface 3 of the test object 1. Even if such a medium lies between them, behavior of ultrasonics on the surface 3 of the test object described belowwill not change substantially.

First, it is specified in FIG. 2 that the transducer 72 has a width of W and a distance between the center of the transducer 72 and the surface 3 of the test object 1 is P1. As long as a transducer having ordinary structure is used as the transducer 72, a main beam of the transducer 72 transmits along the center line of the transducer. However, the main beam of the transducer does not maintain that direction and is refracted when crossing the surface 3 of the test object 1. In FIG. 2, the angle of incidence of an ultrasonic (to be exact, a main beam) transmitted from the transducer 72 upon the surface 3 of the test object 1 is shown as $\alpha$, and the direction of transmission of the ultrasonic after the refraction, namely, an angle of refraction is shown as $\theta s$. Therefore, when viewed from the inside of the test object, an ultrasonic transmitted from the transducer 72 looks as if it were not transmitted from an actual location of the transducer 72, but from a position O which is on the ultrasonic transmitting direction inside the test object 1. In other words, it seems that there is an artifact of the transducer 72 (an apparent transducer 72A) at the position O. A distance P1s between the surface 3 of the test object 1 and the position O of the apparent transducer 72 can be computed from the distance P1 according to Snell's Law, based on the transmitting velocity of the ultrasonic before and after an incidence of the ultrasonic into the surface of the test object 1. Also, the width Ws of the apparent transducer 72A can be computed from a width W according to Snell's Law, based on the transmitting velocity of the ultrasonic before and after an incidence of the ultrasonic into the surface of the test object 1.

Such a situation does not substantially change when an other medium intervenes between the probe 7 and the surface 3 of the test object 1. Further, please note that in the following explanation, the term "ultrasonic transmitting position" does not mean an actual position of the transducer 72, but its apparent position O. Further, as well-known as the Snell's Law, an angle of refraction varies depending on the transmitting velocity which varies depending on a difference in mode of wave, for example, whether it is a longitudinal wave or a transversal wave. Therefore, the angle of refraction $\theta s$, a transmitting direction of ultrasonics inside the test object 1, and the position O of the apparent transducer 72A vary depending on the mode of ultrasonic. This is pertinent to a part of the effect of the present invention. A reference symbol Hs given in FIG. 2 represents a height of the position O from the surface 3 of the test object 1.

Also, in FIG. 1, a scanning mechanism 9 is a mechanism for shifting the probe 7 in a prescribed direction along with the surface 3 of the test object. The scanning mechanism 9 is controlled by a control signal which is transmitted from a controller 81 in an ultrasonic transceiver via a position detector 87. The scanning mechanism 9, together with the probe 7, composes an angle scanning type ultrasonic probe. The angle scanning type ultrasonic probe can be realized not only by the arrangement in which the inside of the test object 1 is scanned by an ultrasonic transmitted from the probe being physically shifted, but also by other arrangements, for example an arrangement in which a plurality of ultrasonic transducers located side by side are selectively excited, as shown in FIGS. 3 and 4.

Figure 3:
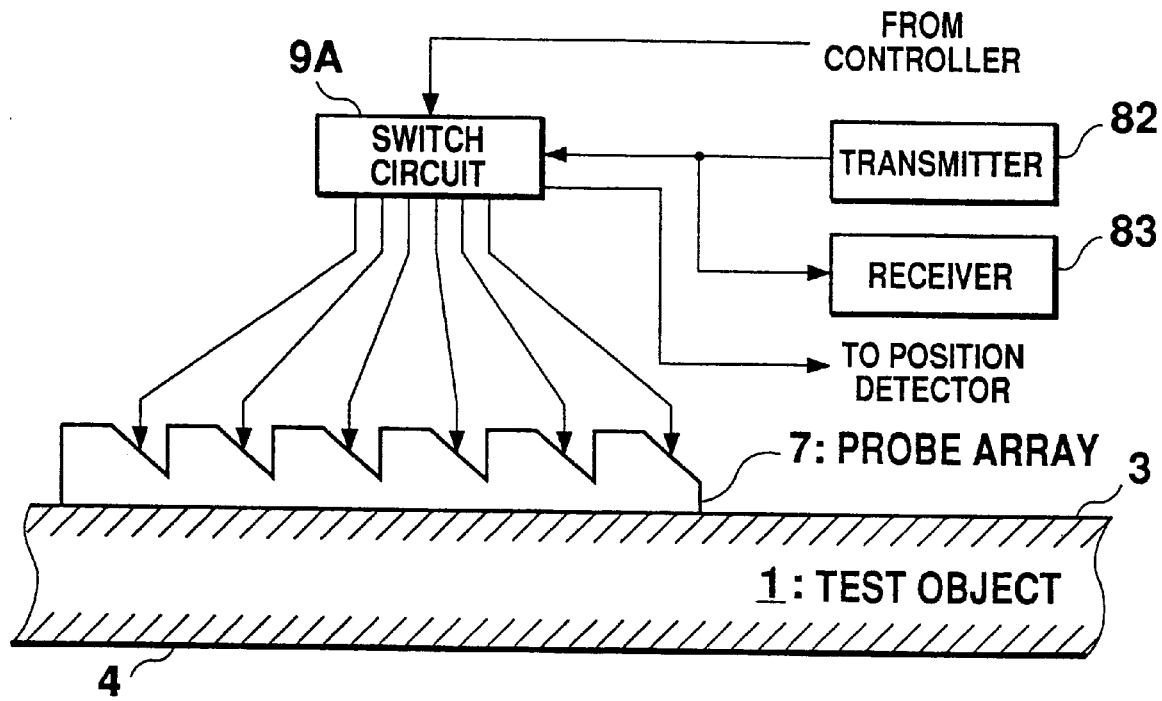
FIG. 3 is a block diagram showing an arrangement of the present invention provided with a probe array and a switch circuit.
Figure 4:
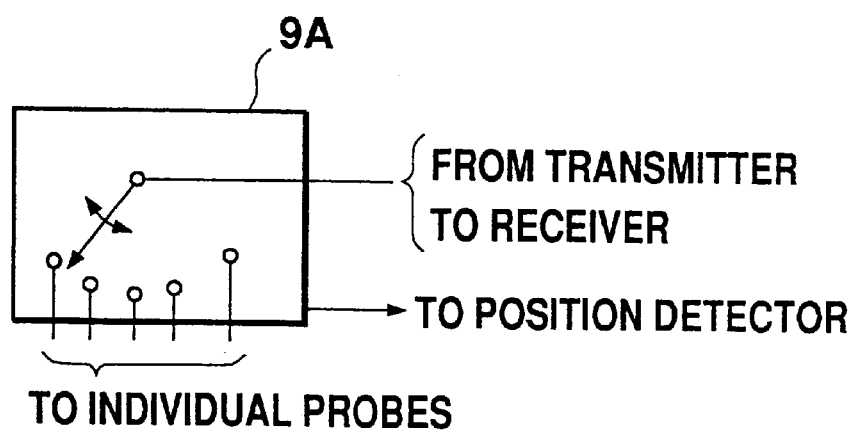
FIG. 4 is a circuit diagram showing the function of the switch circuit.

As shown in FIG. 3 a probe 7 is provided as a form of a probe array having a long wedge and transducers arranged thereon, and with a switch circuit 9A. The wedge has a plurality of cut portions aligned in parallel and with a predetermined horizontal pitch. Each of the transducers is fixed on corresponding one of cut portions to transmit and receive ultrasonics from and to the test object 1, and are designed so as to have same characteristics, such as main beam center direction, angle of refraction, etc. The switch circuit 9A selectively connects, in response to a control signal from the controller 81, the transducers to a transmitter 82 and a receiver 83 and supplies a transmitting position signal specifying a transducer now in use to a position detector 87. The switch circuit 9A may be implemented as a mechanical switch shown in FIG. 4, or as an electronic switching element. The probe array may be implemented as a plurality of individual probes each having a form shown in FIG. 2 and arranged in a holder, to reduce wedge shape complexity and thus the cost of manufacturing or forming the wedge. Since a user may change the number of transducers simply by changing the number of transducers in the holder, it is easy to carry out the measurement in compliance with the thickness of the test object 1, the scanning pitch, the scanning area, etc. Alternatively, the probe array may be implemented by single ceramics wedge having a plurality of cut portions, to reduce the number of components and the number of manufacturing steps.

The position detector 87 is a member for indirectly detecting a present ultrasonic transmitting position O in the angle scanning type ultrasonic probe. Namely, in the angle scanning type ultrasonic probe having a mechanical or an electronical scanning function, the position detector 87 detects the actual position of the probe 7 and convert the detected position to apparent position O. It may be considered that as the position O varies depending on the mode of ultrasonics, the position of the probe 7 is not a sufficient factor to specify the position O. However, it should be noted that, by selecting one out of a plurality of modes, for example a transversal wave of a specified mode, as a mode for the flaw detection of the inside of the test object using the probe 7 (to be more precise, the transducer 72). An angle of refraction θs to be mainly used will be determined, whereby the position O of the apparent transducer 72A can be specified from the actual position of the probe 7 or the transducer 72, on the basis of geometrical relation of the position.

The ultrasonic transceiver 8 has a transmitter 82 for outputting transmitting signals to the probe 7 and a receiver 83 for inputting received signals from the probe 7. The transmitter 82 and the receiver 83 are controlled by the controller 81. First, the transmitter 82 generates a transmitting signal according to the modulation system to be used and waveform and timing of signal set by the controller 81, and then provides the signal to the probe 7 which carries out an electroacoustic conversion of the signal and transmits thus-obtained ultrasonic produced to the surface 3 of the test object 1. The probe 7 further carries out an acoustoelectric conversion of a reflected ultrasonic which arrives from the inside of the test object 1 via the surface 3, to provide a received signal to the receiver 83.

After processing such as an amplification of the received signal, the receiver 83 provides the signal to an A/D converter 84 which converts the received signal into a digital signal, according to a command from the controller 81, and then provides the signal to a signal processor 85. The signal processor 85 carries out a prescribed process of the digital received signal basing on the control signals and various data given by the controller 81 and the position O detected by the position detector 87, to generates a video signal to be supplied to a display device 86. According to the video signal generated, the display device 86, under the control of the controller 81, displays on its screen an image which shows existence or nonexistence, its location, size, configuration, posture, or the like of the discontinuity 6 in the test object 1, with characters or the like.

In FIGS. 1 and 3, numeral 4 represents the back of the test object 1. Also in this drawing, the discontinuity 6 which exists within a so-called "0.5 skip section" is shown as an example. However, it is also possible to design the device such that the discontinuity 6 outside the 0.5 skip section can be detected. The 0.5 skip section is a range in which ultrasonics can travel without going through any reflection from the back 4.

A FIRST EMBODIMENT

Figure 5:
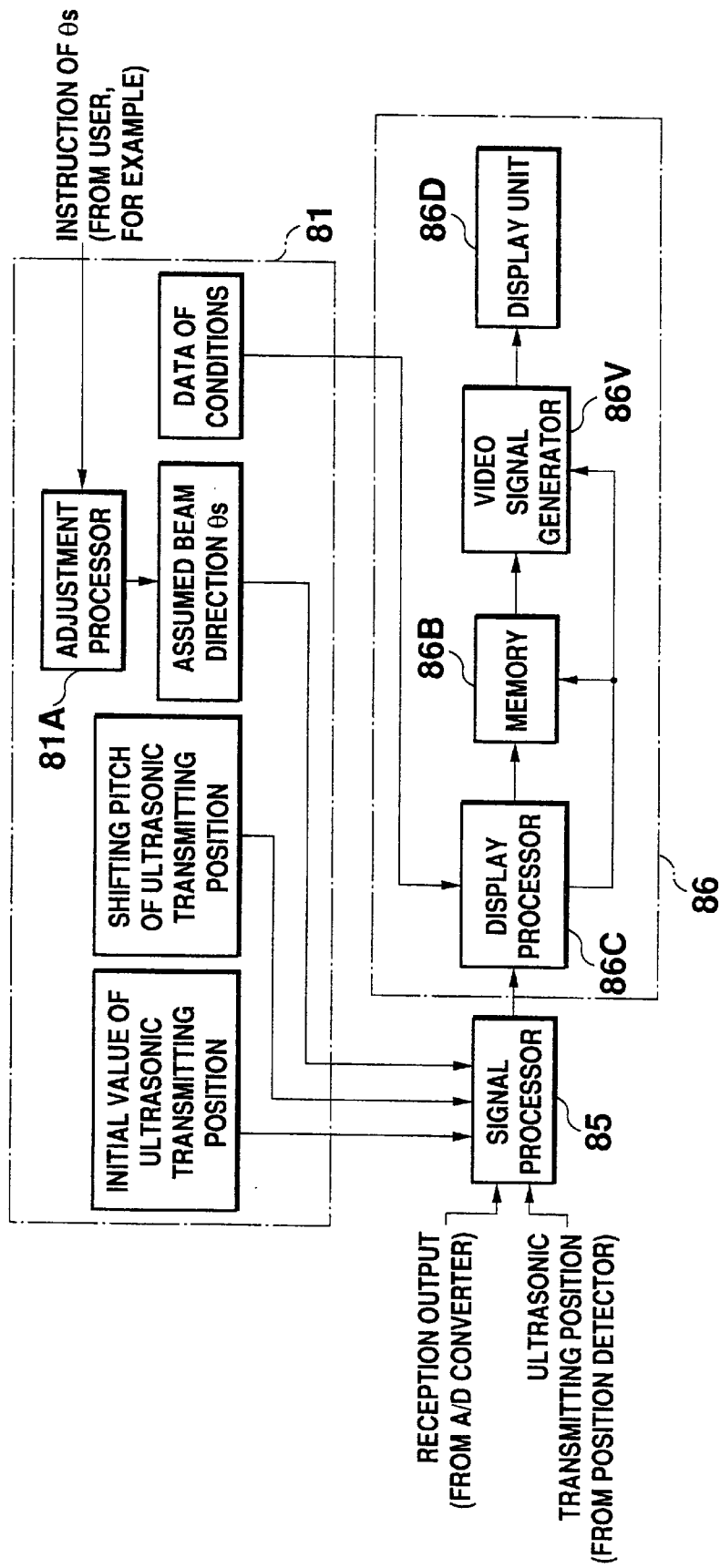
FIG. 5 is a block diagram showing functions of a controller and a display device in a first embodiment of the present invention.
Figure 6:
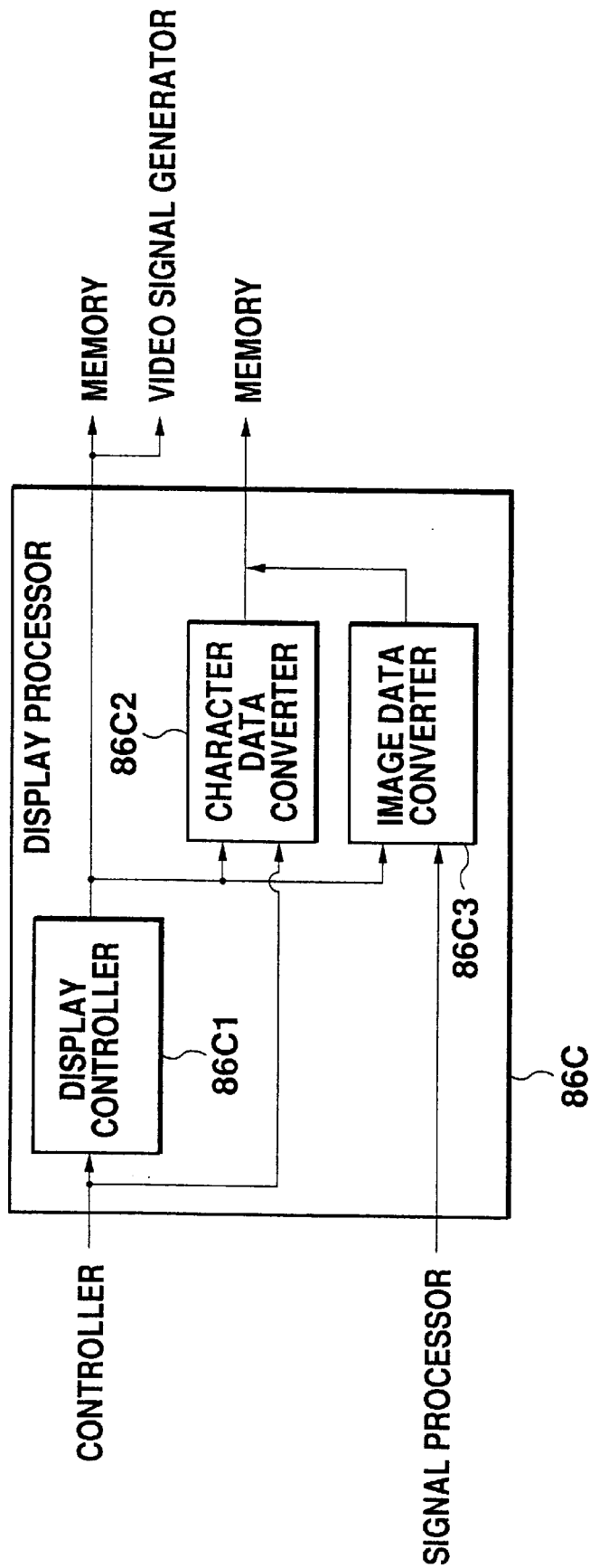
FIG. 6 is a block diagram showing functions of a display processor.

FIGS. 5 and 6 show functional arrangement of an ultrasonic transceiver, especially a display device 86 for displaying an outcome of the signal processor 85 in images and/or characters, according to a first embodiment of the present invention. In a display device 86, 9 display unit 86D such as a television monitor, a liquid crystal display, or the like is provided, to display images or characters according to a video signal from a video signal generator 86V. The video signal generator 86V in response to display control signals from a display processor 86c, reads out one by one display data stored in the memory 86B, converts the data into signals such as composite signal or RGB signal which can be displayed on the display unit 86D, and supplying it as the display signal to the display unit 86D. The memory 86B stores character data and image data written by the display processor 86C, in accordance with a display window arrangement which is instructed by a display control signal from the display processor 86C. In reply to control signals indicating various conditions such as flaw detection condition, signal processing condition or image processing condition from the controller 81, the display processor 86C converts into display data received from the controller 81 an outcome of the signal processor 85, then writes the display data in the memory 86B, and also outputs display control signals for controlling the memory 86B and the video signal generator 86V.

Figure 15:
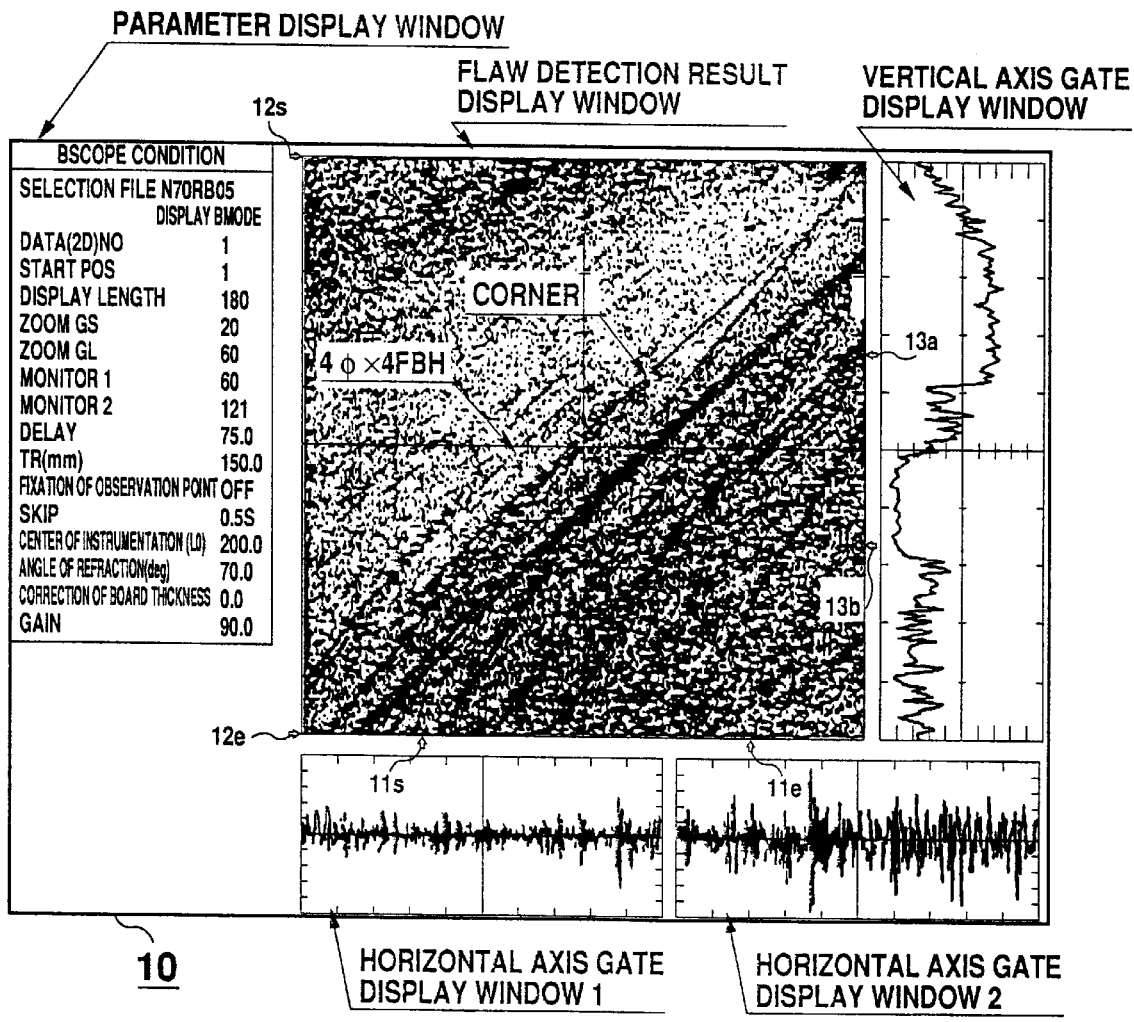
FIGS. 15 and 16 are hard copies of screens which show a B scope formed using the sample of FIG. 13 and a modified B scope formed according to the first embodiment, respectively.

Further, a character data converter 86C2 in the display processor 86 converts the various conditions received from the controller 81 into, for example, character data which is displayed in a parameter display window of FIG. 15 and then outputs the character data to the memory 86B in reply to display control signals from a display controller 86C1. An image data converter 86C3 converts an outcome of the signal processor .85 into image data, based on the display control signals from the display controller 86C1, and then outputs the image data to the memory 86B. The image data described above is, for example, a one-line AC waveform display which is displayed in a horizontal axis gate window 1 of FIG. 15, a section display in which a reception level is displayed in a color tone or a gradation as it is displayed in a flaw detection result display window of FIG. 15, or a profile display of a reception level at every angle of reception as it is displayed in a vertical axis gate window 1 of FIG. 15. A display controller 86C1, by supplying display control signals in reply to control signals from the controller 81, controls the method used in the character data converter 86C2 for converting the various conditions into character data, controls the method used in the image data converter 86C3 for converting an outcome of signal processing into image data, controls a memory space arrangement of display data related to the arrangement of images in the memory 863, and controls the method of generating display signals which is performed by the video signal generator 86V.

The signal processor 85 modified reception signals provided from the A/D converter 84, namely, signals showing reception outputs of the probe 7 basing on an initial value of the ultrasonic transmitting position, an ultrasonic transmitting position shifting pitch and an assumed beam direction θs from the controller 81, and an ultrasonic transmitting position O which is detected by the position detector 87. This modification is executed by giving a command on a write address control for writing a reception output in the memory 86B to the display processor 86C, specially the display controller 86C1. Note that, although the label θs is used, the assumed beam direction differs from the angle of refraction. The assumed beam direction is angle information to be used in the signal processor 85 and is adjustable. For instance, users may adjust the assumed beam direction and search the actual main beam center direction.

Modification performed by the display processor 86C in response to the command from the signal processor 85 is a process for displaying a modified B scope on a screen of the display unit 86D, especially in its display window. More specifically, if a reception output is written in the memory 85B without going through the modification by the signal processor 85 and a video signal is generated basing on the stored reception output, a conventional B scope can be obtained. In this embodiment, the signal processor 85 carries out modification of the reception output for the purpose of converting the B scope into the modified B scope. A difference between the conventional B scope and the modified B scope in this embodiment will be subsequently described.

Figure 7:
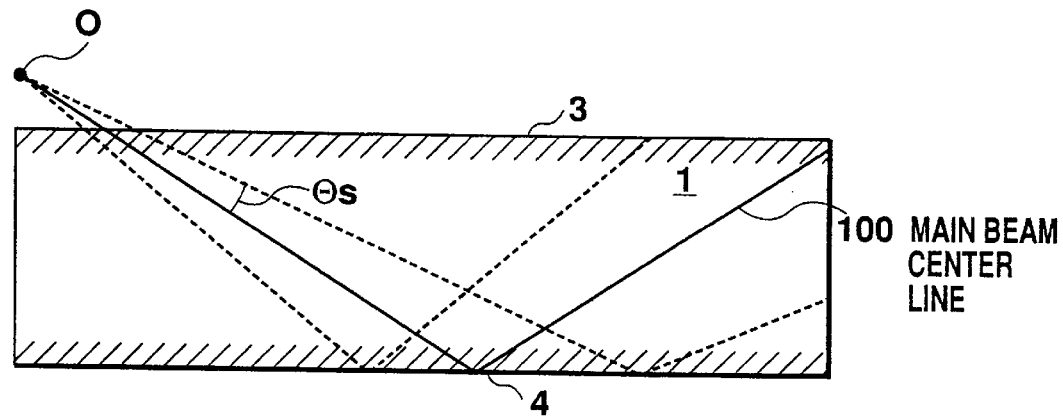
FIG. 7 is a conceptual drawing which shows a main beam center line and probe width.

The ultrasonics from the ultrasonic transmitting position spreadtosomeextent. More specifically, as shown by dashed lines, the main beam of the probe 7 or its transducer 72 usually spreads out from the center line 100 which is shown by a solid line in FIG. 7. A reference symbol Θs in FIG. 7 represents the width of the main beam. The beam width Θs is defined by two directions each of which has, for example, gain of −3 dB relative to reception gain of the main beam center line 100. However, the beam width Θs need not always be defined by the directions of 3 dB down. It can be defined by other reference value, for example 6 dB down, 9 dB down, 12 dB down, or the like.

Figure 8:
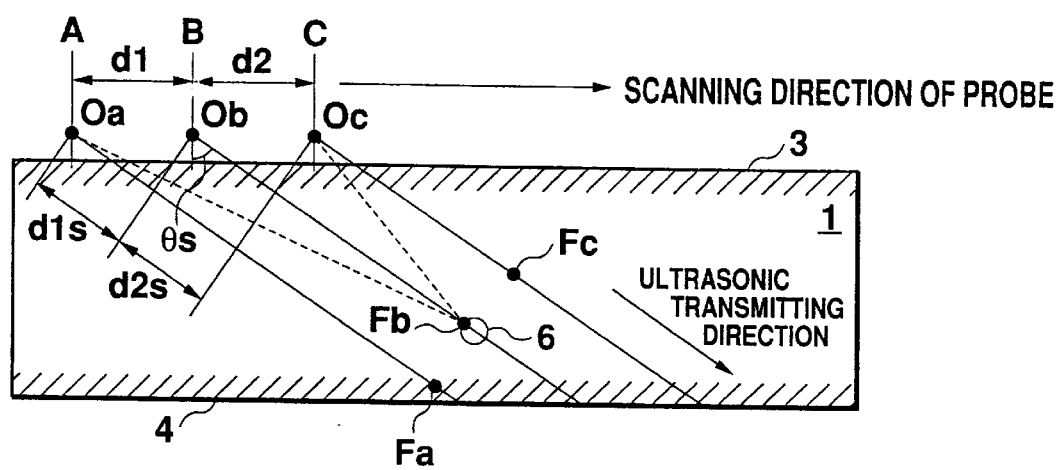
FIG. 8 is a conceptual drawing showing the change of apparent location of discontinuity observed from an ultrasonic transmitting position which is shifted in succession.

Further, as it is the case of this embodiment when the inside of the test object 1 is scanned by ultrasonics by moving the probe 7 along the surface 3 of the test object 1, the beam width Θs becomes influential to the result of flaw detection. For example, as shown in FIG. 8, let it be supposed that at the ultrasonic transmitting position Ob an echo traveled along the main beam center line 100 from the discontinuity 6 is received. If the beam width Θs of the main beam is as narrow as it is considered to be substantially zero, it will be impossible to receive echoes from the discontinuity 6 at positions Oa and Oc with shifts d1 and d2, respectively, to the position Ob along the scanning direction of the probe 7. In actual, since the width of the main beam Θs is wide to some extent, it will be possible to receive an echo from the discontinuity 6 even at the position Oa or the position Oc. However, at the positions Oa and Oc, the position of the discontinuity 6 can not be detected accurately since the echoes look like coming from positions Fa and Fc, respectively. These positions are on main beam center lines at respective positions Oa and Oc and being OaFb and OcFb distant from the respective position Oa and Oc, where the position Fb is an actual position of discontinuity 6 or source of the echo which is caught at the position Ob. Further, echoes received at the positions Oa and Oc have levels comparatively lower than that of echoes received at the position Ob since they are received from a direction which slightly deviates from the main beam center line 100. Therefore, in addition to an echo Fb which is received when the discontinuity 6 is present just on the main beam center line 100, an echo Fa and an echo Fc are displayed as images representing the discontinuity inside the test object 1, when the probe 7 scans the test object 1 by ultrasonics while moving along the surface 3 of the test object 1.

Here, it should be noted that respective distances between the discontinuity 6 and the position Oa, Ob, and Oc differ. In other words, since the distance d1 lies between the position Oa and the position Ob, and the distance d2 lies between the position Ob and the position Oc, respective time periods required for receiving echoes after transmitting ultrasonics at the positions Oa, Ob, and Oc all differ. More specifically, a distance between the position C and the echo Fb which is observed at the position Ob is longer than a distance between the position Oc and the Fc which is observed at the position Oc by "d2s=dsxsin θs," and a distance between the position Oa and the echo Fa which is observed at the position Oa is longer than a distance between the position Ob and the echo Fb which is observed at the position Ob by "d1s=d1×sine θs."

Figure 9:
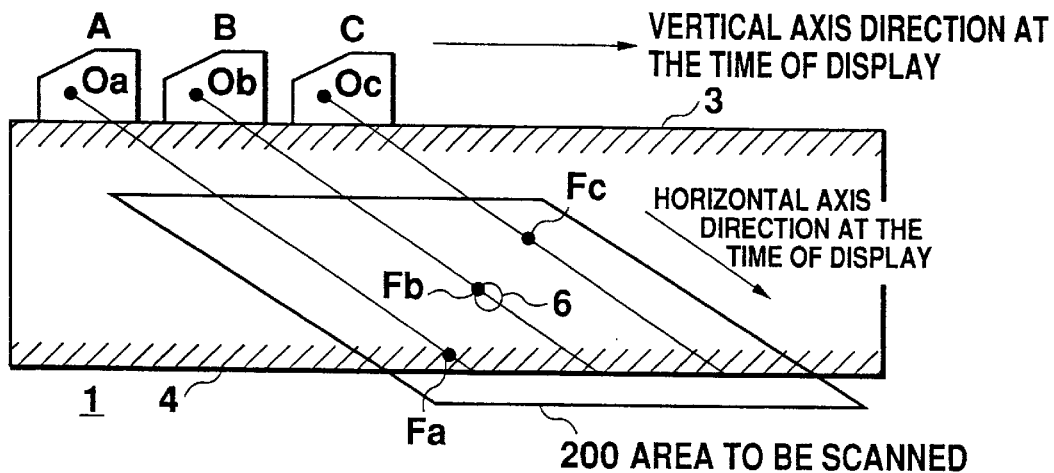
FIG. 9 is a conceptual drawing which shows an area to be scanned for a conventional B scope.
Figure 10:
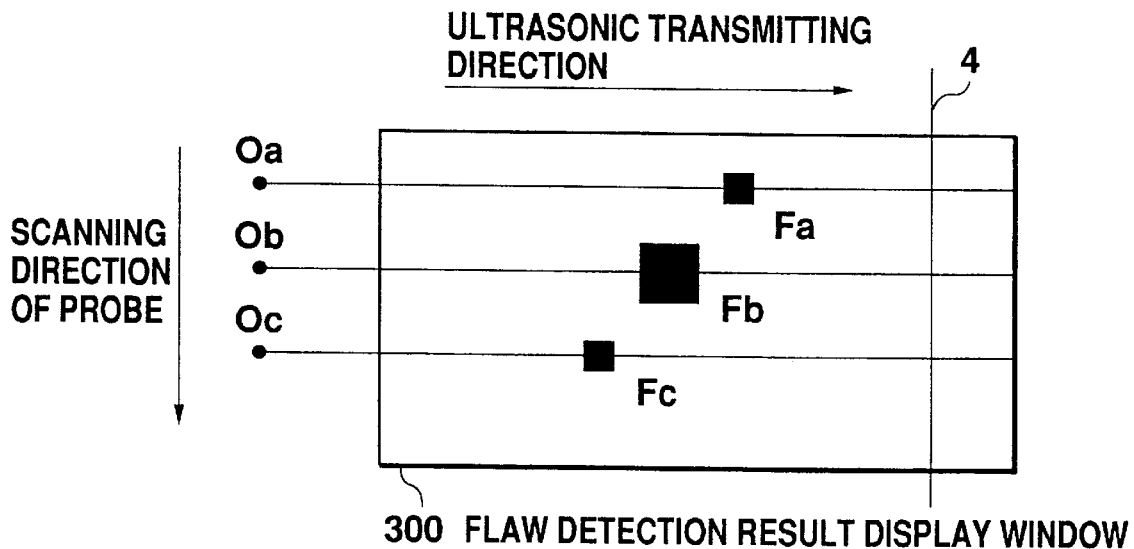
FIG. 10 is a picture view showing an example of B scopes.

In the ultrasonic transceiver for the conventional B scope, a point of time of transmitting an ultrasonic will be displayed on a line parallel to a left edge of a screen (display window), and echoes will be displayed on a horizontal line of the screen (display window), respectively. Therefore, information concerning an area 200 which is shown by a parallelogram in FIG. 9 is displayed in a rectangular flaw detection result display window 300 as shown in FIG. 10. If a display is performed in such a manner, as an apparent distance to the discontinuity 6 varies depending on an ultrasonic transmitting position as shown in FIG. 8, the echoes Fa, Fb, and Fc from a same portion of a same discontinuity 6 will be displayed at mutually different locations which are different in the distances from the left edge of the screen, and in mutually different strength, colors or sizes. Such a display makes it difficult for a user to accurately discern the location, size, configuration, and posture of the discontinuity 6 from the screen. Such a difficulty in discerning the screen will become worse if there is an influence of diffusion or diffraction due to the presence of discontinuity 6, especially if an echo called a diffraction echo or an end echo arises.

Figure 11:
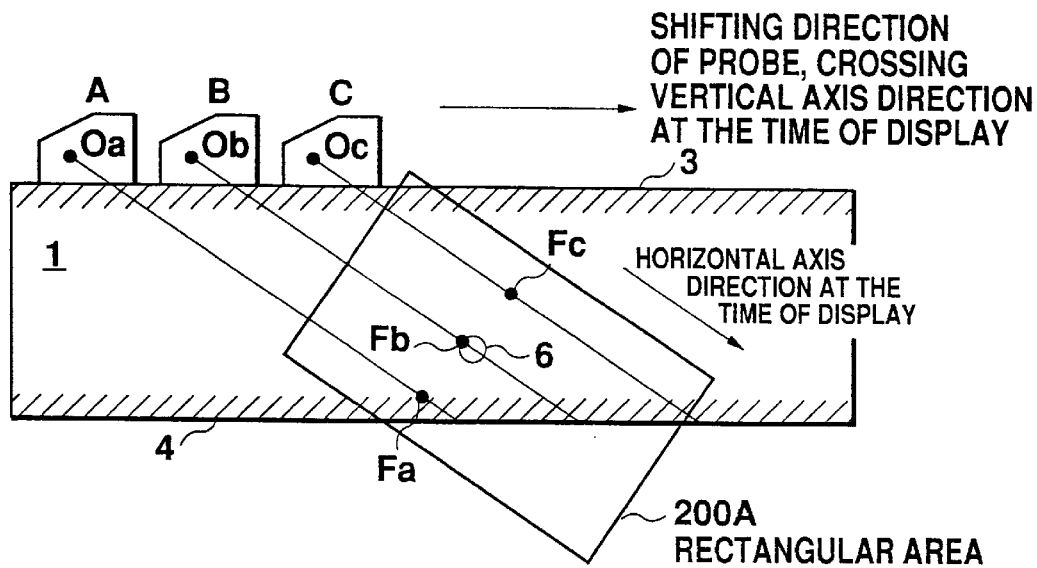
FIGS. 11 and 12 are conceptual drawings which show time axis shifting and the effect thereof, according to the first embodiment in the present invention, at the time of displaying a modified B scope.
Figure 12:
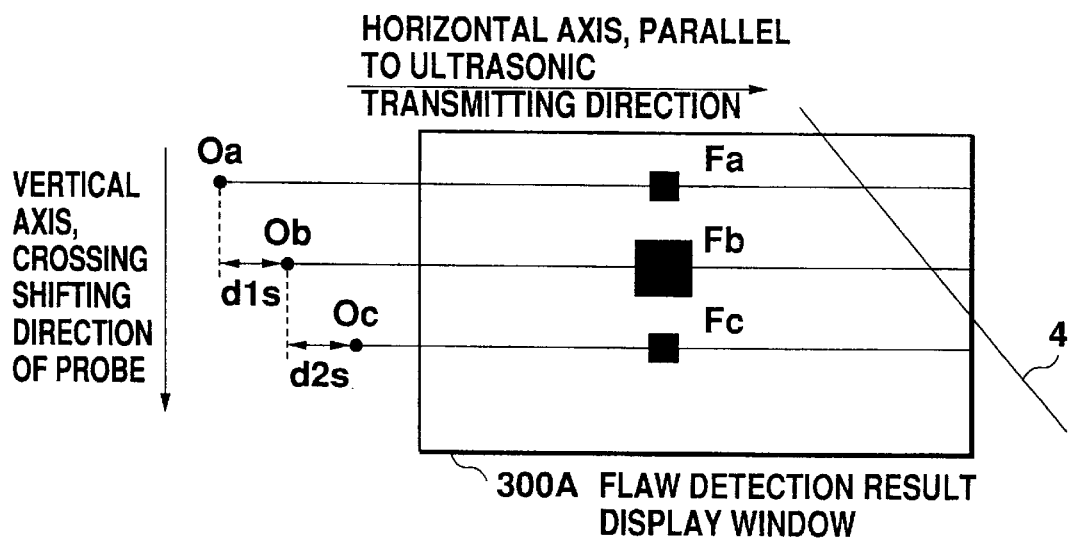

In a process performed by the signal processor 85 in this embodiment, a change of the distance from every ultrasonics transmitting position to the discontinuity 6, which may apparently arise with the change of the ultrasonic transmitting position O is compensated by controlling a write address for reception outputs in the memory 85B, thereby obscurity of the conventional B scope shown in FIG. 10 is reduced or solved. More specifically, by shifting the write address in the memory 85B according to a change d of the apparent distance which is generally represented as "ds=dx sin θs," information concerning a rectangular area 200A in the test object 1 is displayed by the display device 86D, as shown in FIG. 11. In other words, by writing data obtained from this rectangular area 200A to be scanned in the memory 85B while performing the control of the write address described above, a video signal representing a rectangular area 200A is generated basing on display data which is read out from the memory 85B by the video signal generator 85V, and the image of discontinuities in the area 200A is displayed in the rectangular flaw detection result display window 300A. consequently, the obscurity shown in FIG. 10 will not arise and as shown in FIG. 12, it is possible to provide a modified B scope which is useful than the conventional B scope, namely, to provide a modified B scope from which the location, size, configuration, and posture of the discontinuity 6 can be more accurately discerned.

In FIG. 5 described before, data which the signal processor 85 receives from the controller 81 or the position detector 87 are available for the aforementioned process, namely, a process pertinent to the conversion of the B scope into the modified B scope. For example, an initial value of ultrasonic transmitting position provided by the controller 81 is a value of the position O where an ultrasonic is transmitted at the beginning of a series of the conversion. Further, a shifting pitch of the ultrasonic transmitting position is in general form d in the aforementioned equation. Also, an outcome of detection of the ultrasonic transmitting position O which is provided by the position detector 87 is an operation timing of ds in the signal processor 85.

Further, the controller 81 shown in FIG. 5 is provided with an adjustment processor 81A for adjusting in formation concerning an assumed beam direction θs when it is provided to the signal processor 85. As described above, since the actual angle of refraction θs varies depending on the mode of an ultrasonic inside the test object 1, by adjusting data of the assumed beam direction used in the signal processor 85, it is possible to display the echoes Fa, Fb and Fc more definitely in the display window 300A and distinguish them from echoes of other modes more accurately. For example, in a device designed so as to utilize transversal waves, even when the adjustment is not performed, the echo of an indirect ultrasonic which is received by the transducer 72 after the conversion from a transversal wave to a longitudinal wave and again to a transversal wave in the test object 1, is displayed in a different part of the display window 300A as a comparatively weaker image, as compared with the echo of a direct ultrasonic, which is received after transmission without going through such a conversion, namely, after being transmitted as the transversal wave it is. Therefore, it is impossible for a user to mistake an echo pertinent to this mode converted wave for an echo pertinent to a transversal wave, even though a fine adjustment is not performed by the adjustment processor 81A. Moreover, if the assumed beam direction θs is adjusted by the adjustment processor 81A, a probability of arising such a misconception will decrease furthermore. This is one of the characteristic effects of the embodiment in which conversion is carried out basing on the data concerning the angle of refraction.

Figure 13A:
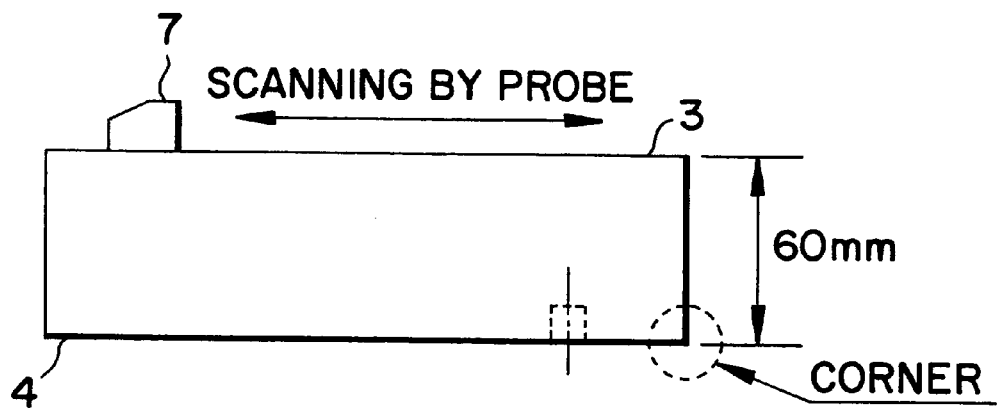
FIG. 13 shows an external appearance of a sample which is used for estimating an effect of the present invention.
Figure 13B:
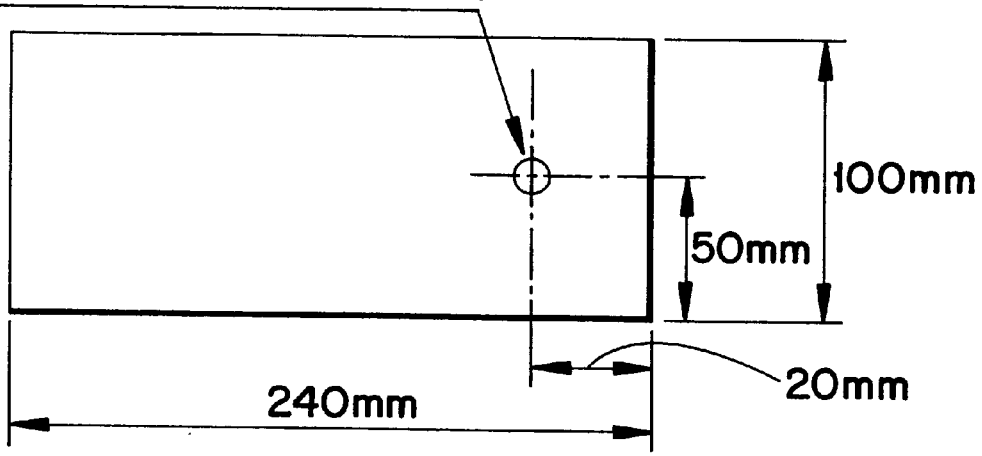
Figure 14:
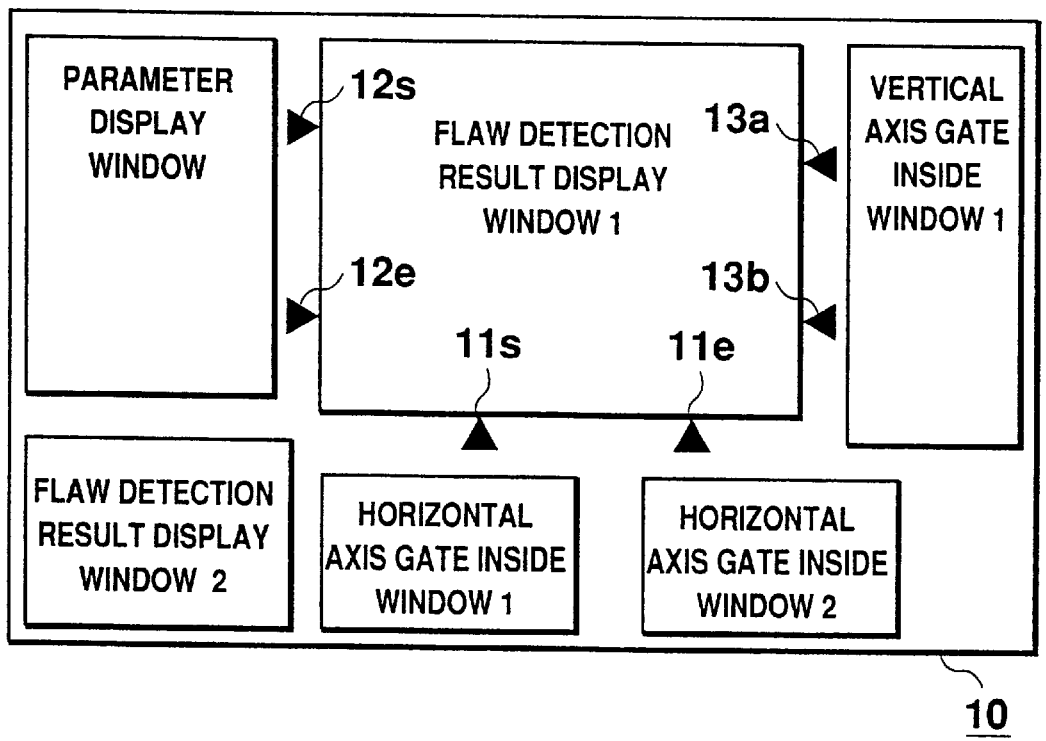
FIG. 14 is a picture view showing an example of display screens in the first embodiment of the present invention.

In FIGS. 13 to 16, an effect of improvement of image quality according to this embodiment is shown. Among these drawings, FIG. 13 shows a configuration of the sample which is used as the test object 1 for the purpose of comparing the conventional B scope with the modified B scope in this embodiment. As shown in this drawing, the sample used as the test object 1 has a 4 mm hole diameter at its bottom and several corners. In FIG. 14, a composition of a screen of the display device 86D in this embodiment is shown. As shown in this drawing, a screen 10 of the display device 86D has, for example, two flaw detection result display windows, two horizontal axis gate inside display windows, a vertical axis gate inside display window, and a parameter display window. The flaw detection result display windows are for displaying the modified B scope shown in FIG. 12. Two windows are provided in order to enable the following usage: to display results of flaw detection of a single test object in two different display modes; to compare results of flaw detection obtained from two types of test objects 1; and to compare results which are obtained by performing two types of signal processes of a reception output obtained from a single test object 1. Also, the parameter display window is for displaying a condition of the flaw detection, a condition of the signal process, a condition of the image process, and the like. The horizontal axis gate inside display windows and the vertical axis gate inside display window are for displaying reception output waveforms in a range which is enclosed by horizontal axis gate markers and a reception output waveform in a section which is enclosed by a vertical axis gate markers. In these drawings, reference symbols 11s and 11e are horizontal axis gate markers, while 11s is a start marker and 11e an end marker. Similarly, reference symbols 12s and 12e are vertical axis gate markers, but 12s is a start marker and 12e an end marker. Further, reference symbols 13a and 13b are probe position designating markers. Two horizontal axis gate inside display windows are provided in the screen 10 of FIG. 14 to display waveforms, frequency characteristics, or the like of reception outputs at respective locations of these probe position designating markers 13a and 13b.

Figure 16:
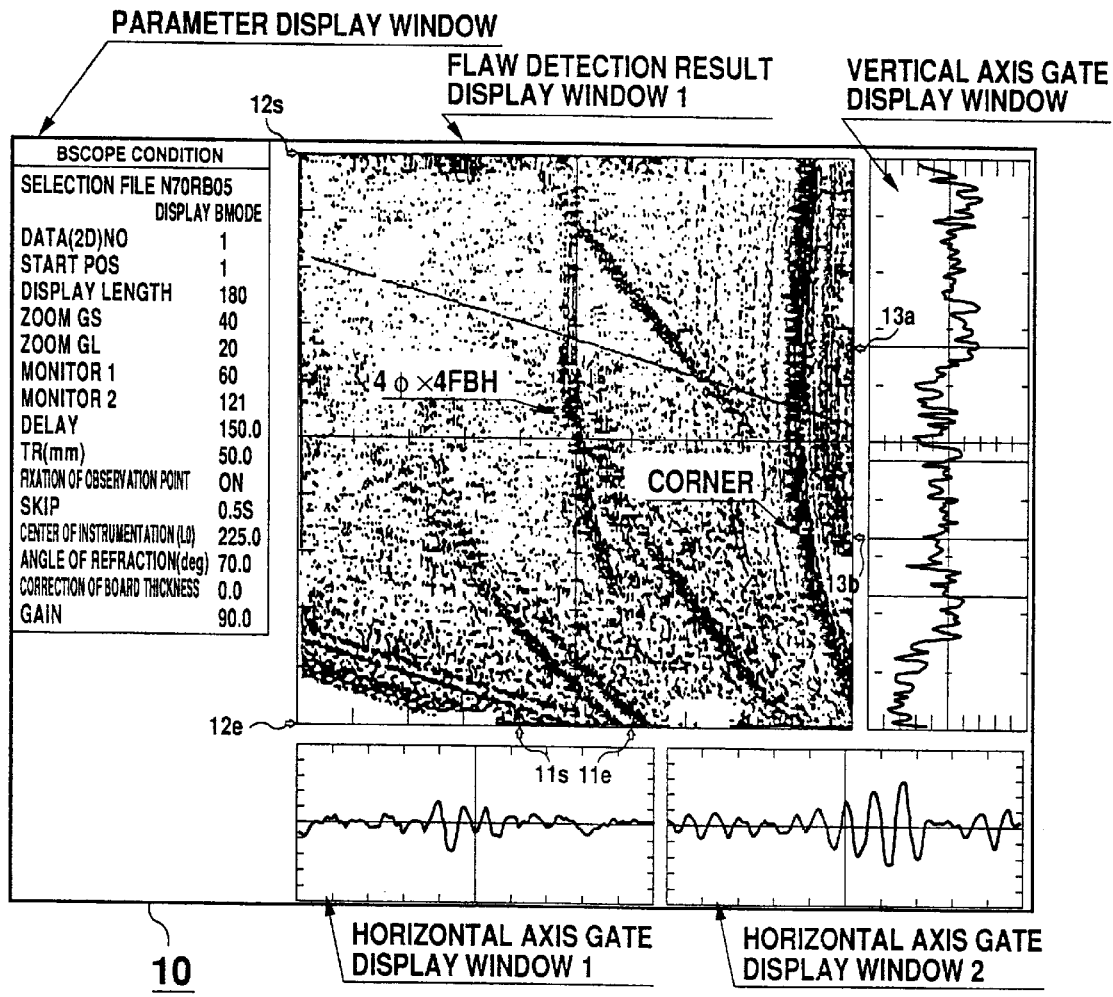

In the experiment using a sample having a shape shown in FIG. 13 was used as the test object 1, a conventional B scope (FIG. 15) is generated using the embodiment screen structure shown in FIG. 14, to enable comparing the modified B scope (FIG. 16) obtained by the present embodiment. As it is obvious when FIG. 15 and FIG. 16 are compared in conventional B scope, it is difficult to discern the corner or the hole of the back 4, each of which is a discontinuity 6, because the level of a background echo (spurious echo) is high, i.e., the signal-to-noise ratio of the conventional B scope is low. On the other hand, in the modified B scope according to this embodiment, the level of a background echo is low and the signal-to-noise ratio is high as shown in FIG. 16, i.e., the corner and the hole are distinguishable from various noises. As a result of comparison of these two scopes by using the same sample shown in FIG. 13, it is proved that according to the present embodiment the locations, size, configurations and postures of the corner and the hole can be easily discerned.

A SECOND EMBODIMENT

Figure 17:
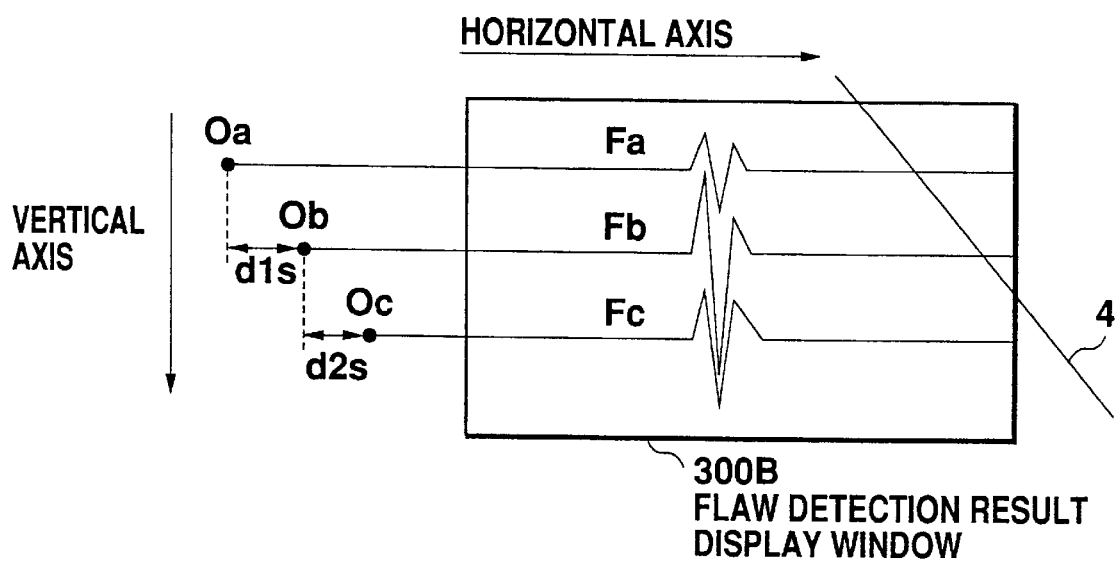
FIG. 17 is a view which shows an example of display windows in a second embodiment of the present invention.

FIG. 17 shows a modified B scope of a second embodiment of the present invention. In the first embodiment described above, the modified B scope is displayed on a screen of the display device 86 in such a manner that the higher received levels echo will be shown by larger image areas. In the second embodiment, an alternating waveform (ondogram) of a reception output obtained at each ultrasonic transmitting position is displayed as is in the display window 300B. Even when such a display is adopted, the same effect as that of the aforementioned first embodiment can be obtained. Moreover, if an ondogram is displayed leaving it intact like the second embodiment, phase data which is contained in an echo from the discontinuity 6 can be displayed in the display window 300B. More specifically, users can know the state of occurrence of a phase inversion, phase interference or the like in the discontinuity 6 or the like, from a waveform which is displayed in the display window 300B. Consequently, characteristics of the discontinuity 6 can be more accurately and precisely discerned.

Further, a mode of display by ondogram which is adopted in the second embodiment can be used together with a mode of display by area which is adopted in the aforementioned first embodiment. More specifically, as the screen 10 shown in FIG. 14 is provided with two flaw detection result display windows, the display mode can be set in such a manner that one flaw detection result display window is used for the display by area and the other flaw detection result display window for the display by ondogram. Setting of this display mode can be controlled by using a display control signal which the controller 81 provides to the display processor 86C. Alternatively, a pseudo color display in which an image to be displayed is colored depending on the level of an echo or the like can be enumerated as other display mode which can be adopted in the present invention.

A THIRD EMBODIMENT

Figure 18:
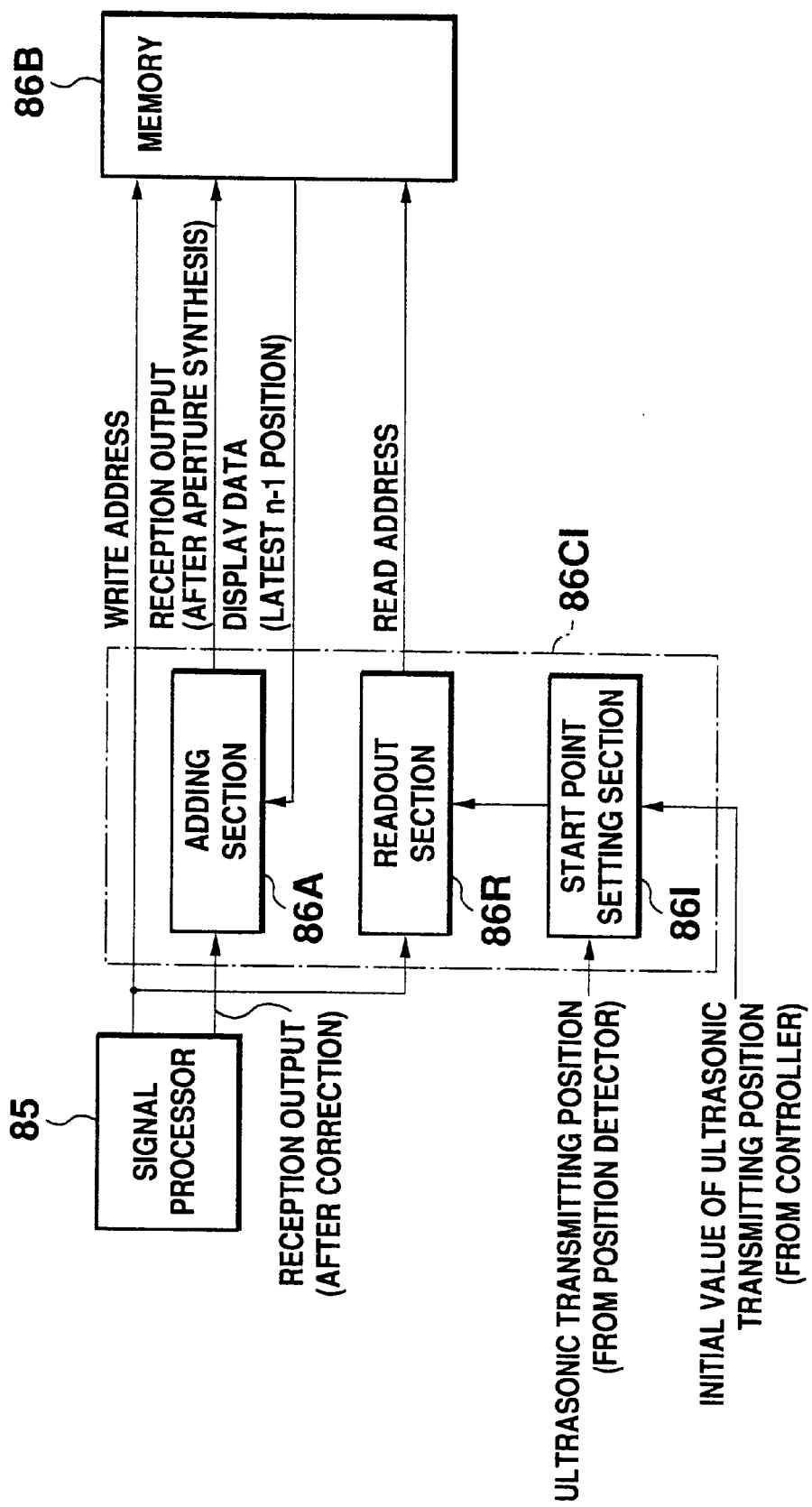
FIG. 18 is a block diagram which shows functions of a display processor in a third embodiment of the present invention. However, portions shown in FIG. 5 are omitted.

In FIG. 18, the constitution of signal processor 85 in a third embodiment of the present invention is shown. in this drawing, portions which are common to FIG. 5 are omitted. As shown in FIG. 18, a display controller 86C1 between the signal processor 85 and the memory 86B functions as an aperture synthesizer in this embodiment. The aperture synthesizer 86C1 has a start point setting section 86I for setting a left edge of the flaw detection result display window, namely a start point, based on an ultrasonic transmitting position O detected by the position detector 87 and an initial point of ultrasonic transmitting position O given by the controller 81; a readout section 86R for determining a read address from the memory 86B basing on the start point determined by the start point setting section 86I and the write address outputted from the signal processor 85; and an adding section 86A for adding display data which is read out from the read address, determined by the readout section 86R, and a reception output which is output from the signal processor 85, the sum of the read out data and the reception output being written into the memory 86B by the adding section 86A. Because of the arrangement described above, the aperture synthesize 86C1 performs so-called aperture synthesis of reception outputs which are outputted from the signal processor 85.

Figure 19:
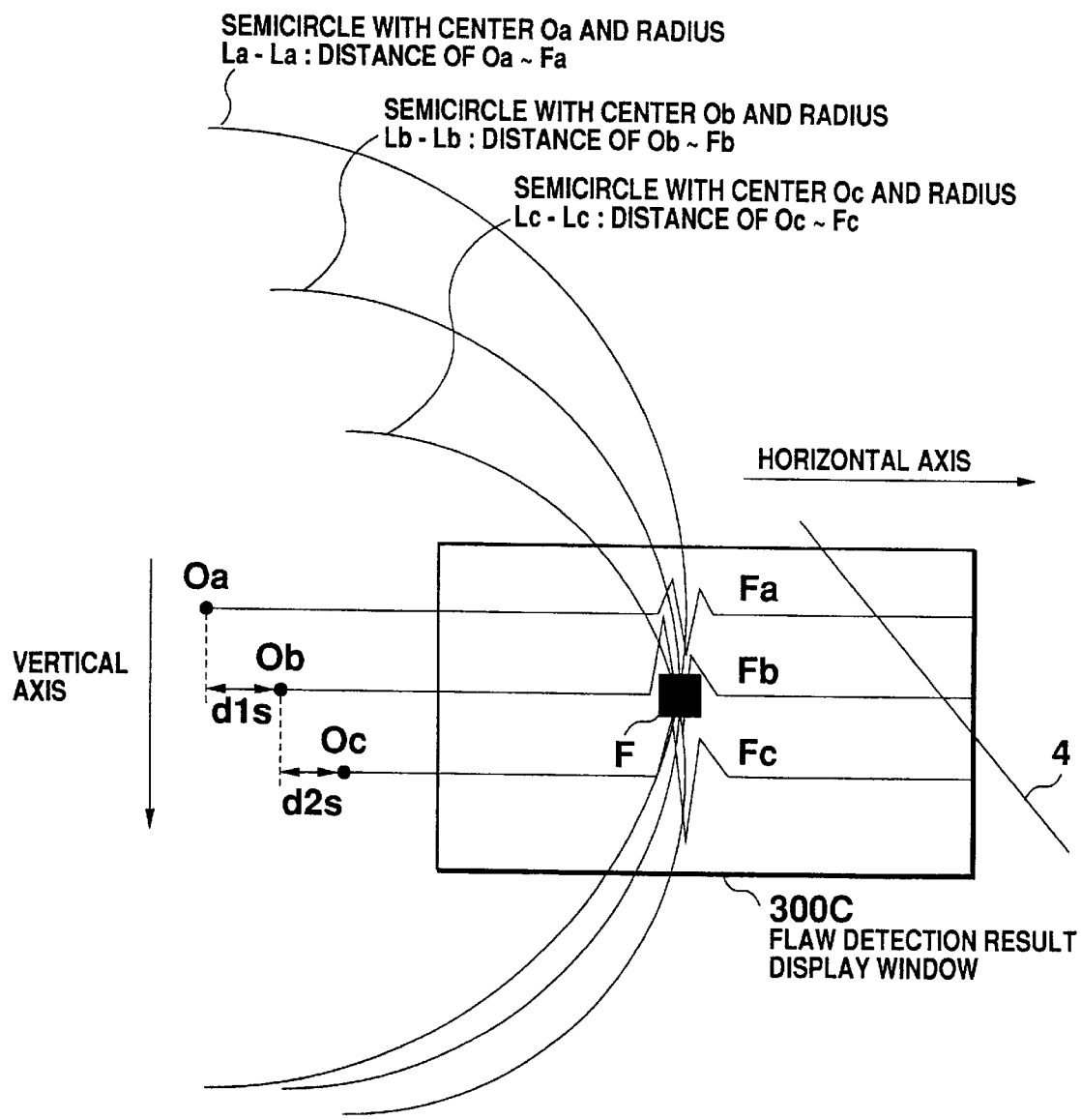
FIG. 19 is a conceptual drawing which shows a principle and an effect of aperture synthesis.

The aperture synthesis performed in this embodiment is a type of line aperture synthesis. For a situation in which, as shown in FIG. 19, the ultrasonic transmitting position O is shifted from a position Oa to a position Ob and further from the position Ob to a position Oc, whereby an echo from the discontinuity 6 can be received at any one of these positions, a reception output which can be obtained at the position Oa contains an echo Fa, a reception output which can be obtained at the position Ob contains an echo Fb, and a reception output which can be obtained at the position Oc contains an echo Fc, respectively, echoes Fa, Fb and Fc representing same discontinuity. Therefore, by summing or accumulating reception outputs which are alike in the distance from respective ultrasonic transmitting positions Oa, Ob, and Oc, and writing the result of the summation in the memory 86B while performing the aforementioned write address control, it is possible to display an image of the discontinuity 6 with enhanced area, color, or waveform on a screen of the display unit 86D. Therefore, the positions can be accurately perceived. More specifically, by reading out from the memory 86B n-1 line of display data each line of which corresponds to one of most recent n-1 lines, summing the display data and the latest reception output which is outputted from the signal processor 85, and then writing them in the memory 86B as n-th line display data in the latest display data (n-th display data), past n-1 lines of reception outputs area accumulated with the latest line of reception output with in which the same-distance data are summed. Therefore, in video signals generated basing on the contents stored in the memory 86, the emphasis falls on echoes from the discontinuity 6.

Due to such a line aperture synthesis, in this embodiment, it is possible to perform an enhanced and focussed display of echoes from the discontinuity 6 in the display window 300C on the screen of the display unit 86D. In other words, it is possible to improve bearing resolution and a signal-to-noise ratio.

A FOURTH EMBODIMENT

Figure 20:
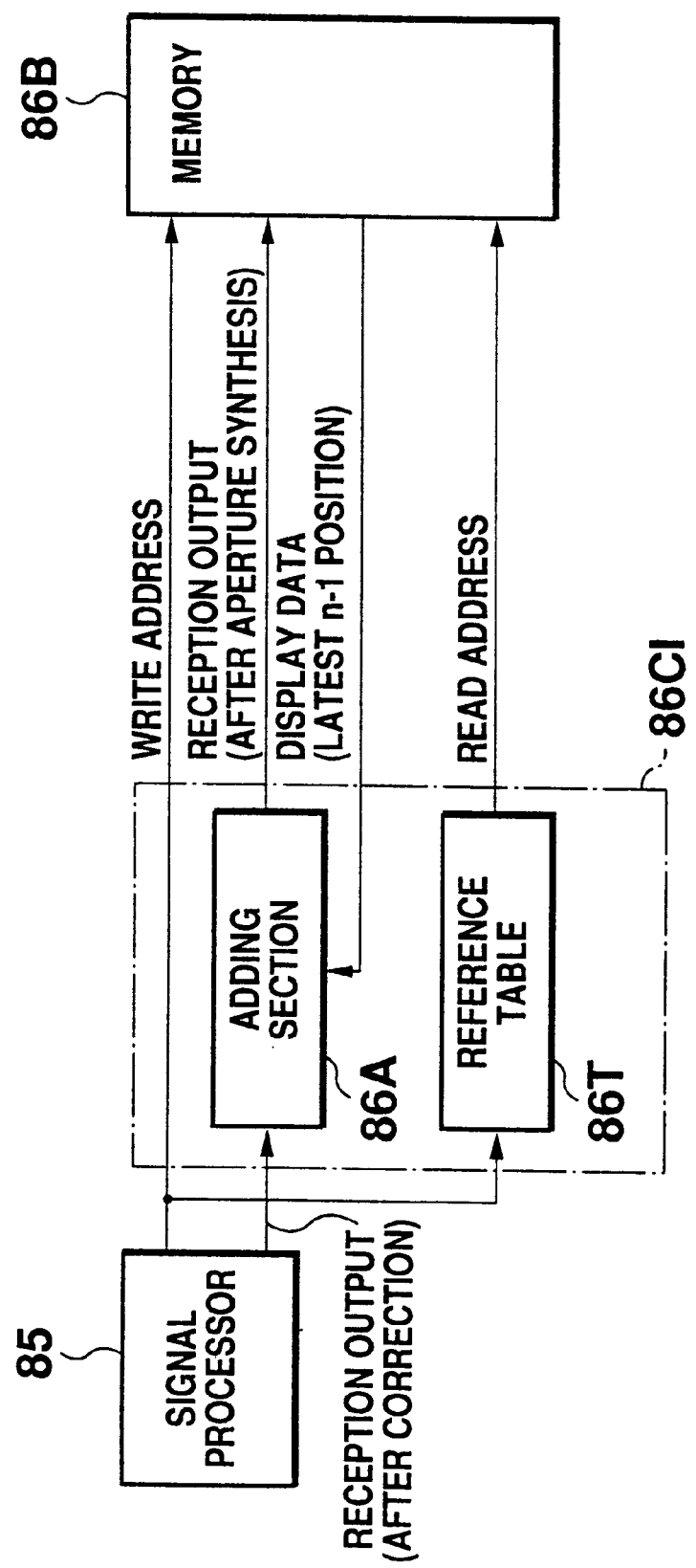
FIGS. 20 and 21 are block diagrams which show functions of display processors in a forth embodiment and a fifth embodiment of the present invention, respectively with portions shown in FIG. 5 are omitted.

In FIG. 20, the arrangement according to a fourth embodiment of the present invention is shown. In this drawing, portions which are common with FIG. 5 are omitted. This embodiment is characterized in that a function which is equivalent to that of the aperture synthesizer 86C1 in the third embodiment is realized by using a reference table 86T. More specifically, in the third embodiment, the start point setting section 86I sets a start point based on an ultrasonic transmitting position O and its initial value, and the readout section 86R sets readout addresses one by one based on write addresses and the start point whereas, in this embodiment., setting of the start point and determination of the readout addresses are performed by using the reference table 86T previously constructed. Thus, the constitution of the aperture synthesizer 86C1 can be simplified, as long as the shifting pitch of the probe and the plane to be scanned by the probe 7 are notified in advance. Therefore, a total processing load on the aperture synthesizer 85 and the display device 86 can be reduced, thereby leading to a high-speed process. In other words, even in such a case that an outcome of the flaw detection performed by using the device of the third embodiment cannot be displayed in real time, if the arrangement of the fourth embodiment is applied, such a problem will be solved.

A FIFTH EMBODIMENT

Figure 21:
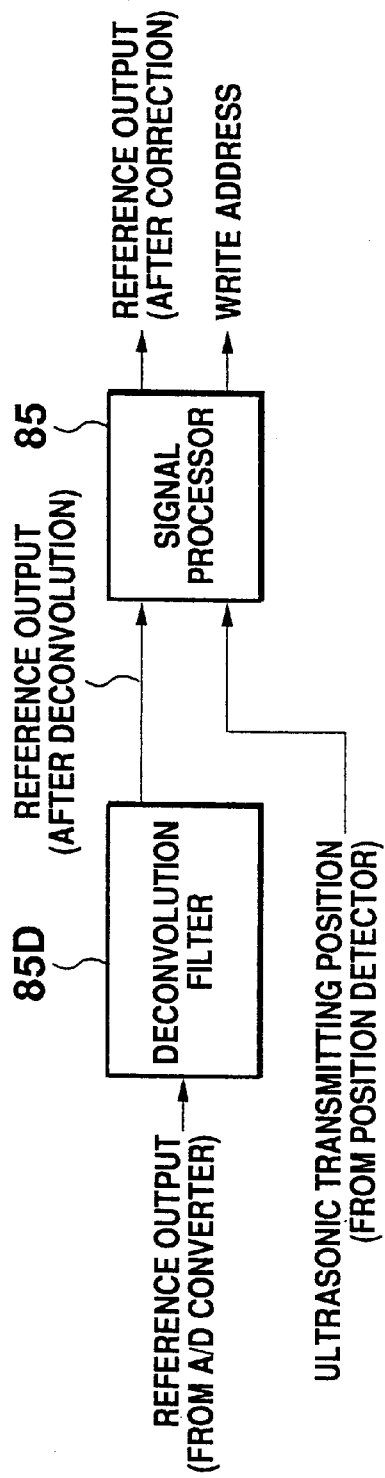

In FIG. 21, functional arrangement of a fifth embodiment of the present invention is shown. However, the portions which are common with FIG. 5 are omitted.

Figure 22:
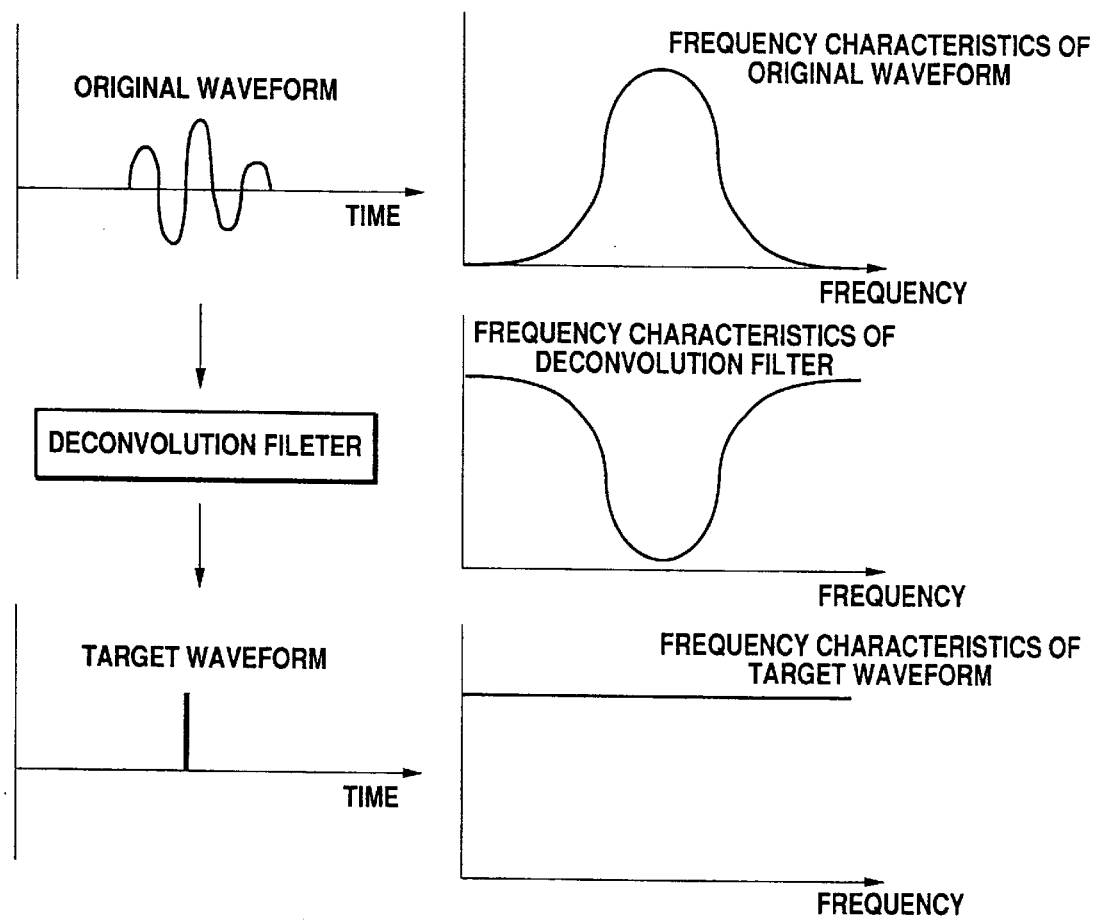
FIG. 22 is a conceptual drawing which shows a principle of deconvolution.

This embodiment is characterized in that the signal processor 85 is provided with a deconvolution filter 85D at the preliminary stage. The deconvolution filter 85D performs the deconvolution process to reception outputs which are provided from the A/D converter 84 and thus provides resultant or deconvoluted reception outputs to the signal processor 85. The deconvolution process to be carried out by the deconvolution filter 85D in the present embodiment is, as shown in FIG. 22, a process for convoluting in reception outputs the characteristics which are reciprocal to characteristics convoluted in signals at the time of transmission and reception of ultrasonics, for example characteristics of the probe 7. More specifically, even if an ideal impulse is utilized as an excitation pulse of the probe 7, due to the presence of the probe's own characteristics and the like, in the strict sense of the word, a reception output will not be an impulse response. However, if the convoluted characteristics including characteristics of the probe 7 are already known, it will be possible to generate a reception output which is a nearly ideal impulse response by convoluting the reciprocal characteristics in the reception output. Thus, in this embodiment, by performing a deconvolution process of the reception output, the reception output can have a response waveform which is closer to ideal. In other words, the time resolution, namely, range resolution can be improved.

A SIXTH EMBODIMENT

Figure 23:
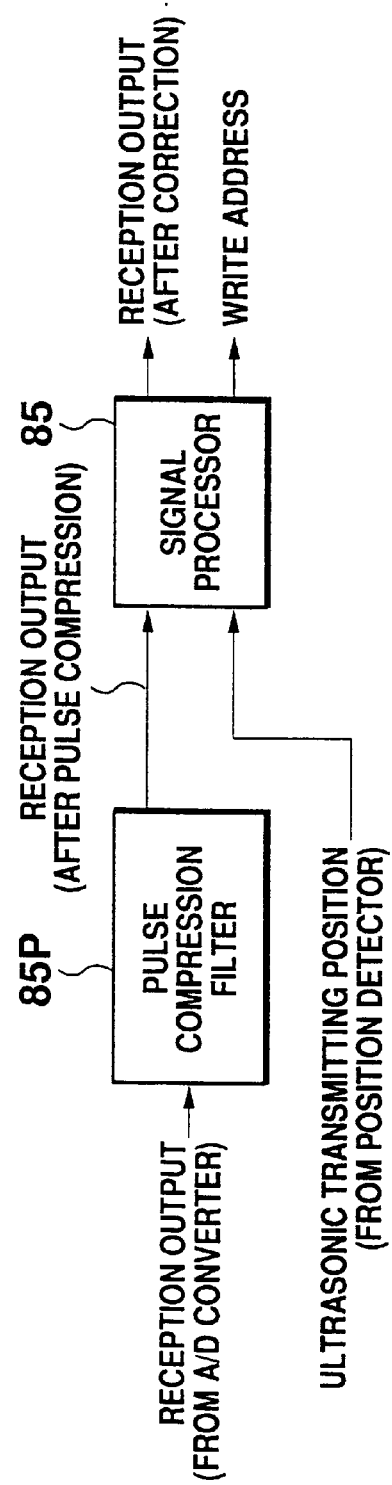
FIG. 23 is a block diagram which shows functions of a display processor in a sixth embodiment of the present invention. However, portions shown in FIG. 5 are omitted.
Figure 24:
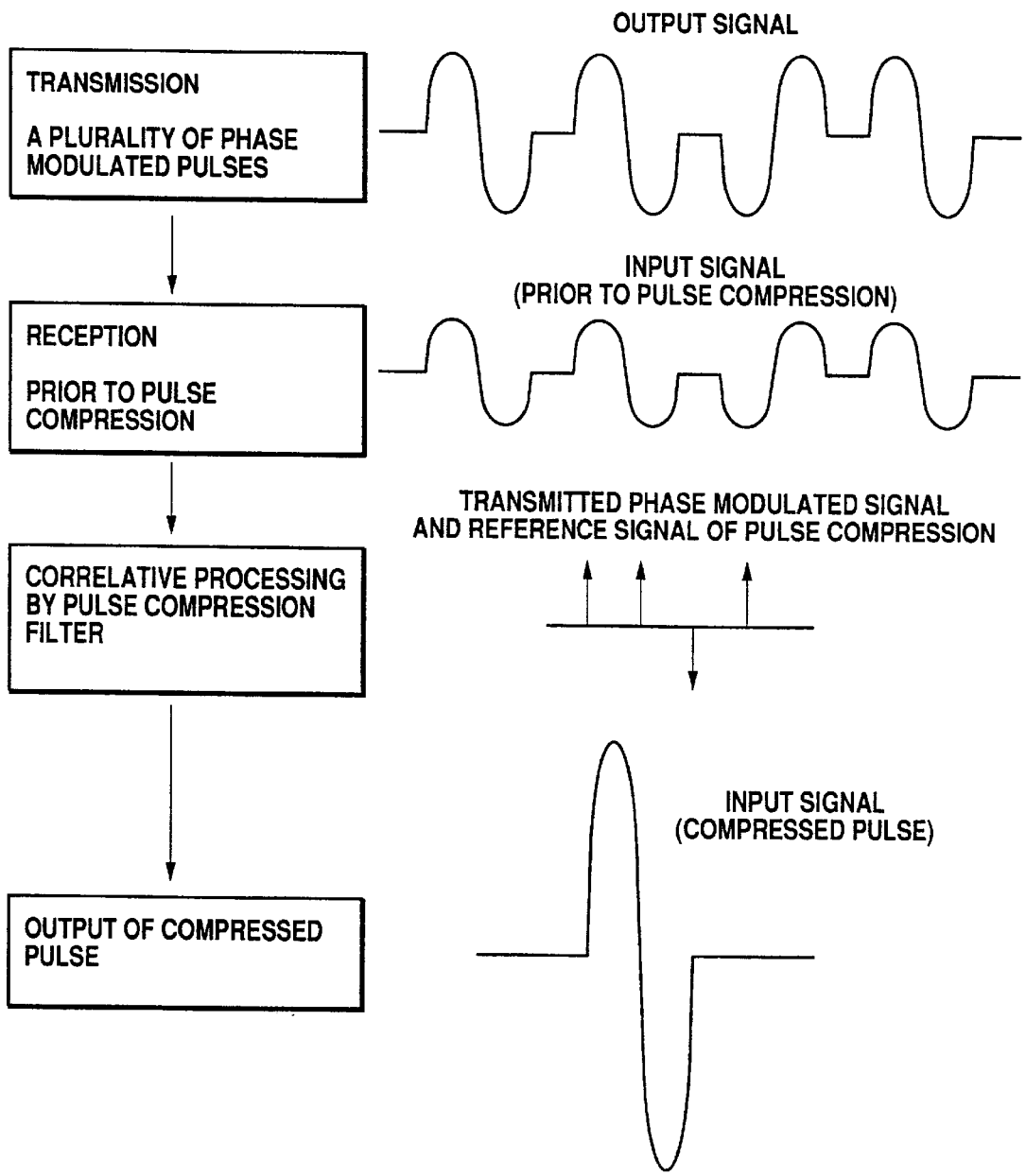
FIG. 24 is a conceptual drawing which shows a principle of pulse compression.

In FIG. 23, functional arrangement of a sixth embodiment of the present invention is shown. In this drawing, portions which are common with those of FIG. 5 are omitted. This embodiment is characterized in that prior to modification to be performed by the signal processor 85, pulse compression is carried out on a reception output by a pulse compression filter 85P. Pulse compression in this embodiment means, for example, a process as shown in FIG. 24. In this drawing, since a phase modulation is effected by the transmitter 82 to signals which are to retransmitted from the probe 7, reception outputs of the probe 7 contain phase modulation components. The pulse compression filter 85P derives a correlation between a modulation signal, used for the phase modulation in the transmitter 82, and a reception output, provided through the A/D converter 84. Thus, phase modulation components are removed from the reception output, while energy which has been dispersed in a plurality of pulses due to phase modulation is concentrated in a single pulse. Consequently, this embodiment can have an effect of the pulse compression, namely, an effect of improving a signal-to-noise ratio of the reception output.

SEVENTH, EIGHTH, NINTH, TENTH, ELEVENTH, TWELFTH, AND THIRTEENTH EMBODIMENTS

The line aperture synthesis performed in the third and fourth embodiments, the deconvolution in the fifth embodiment, and the pulse compression in the sixth embodiment, which are described above, can be performed in combination. For example, in a seventh embodiment shown in FIG. 25 and an eighth embodiment shown in FIG. 26, the deconvolution and the line aperture synthesis are carried out together. In the seventh embodiment, there is provided, in the same manner as the third embodiment, an aperture synthesizer 86C1 which has the start point setting section 86I and the readout section 86R. In an eighth embodiment shown in FIG. 26, there is provided an aperture synthesizer 86C1, which has the reference table 86T, in the same manner as the fourth embodiment.

Figure 25:
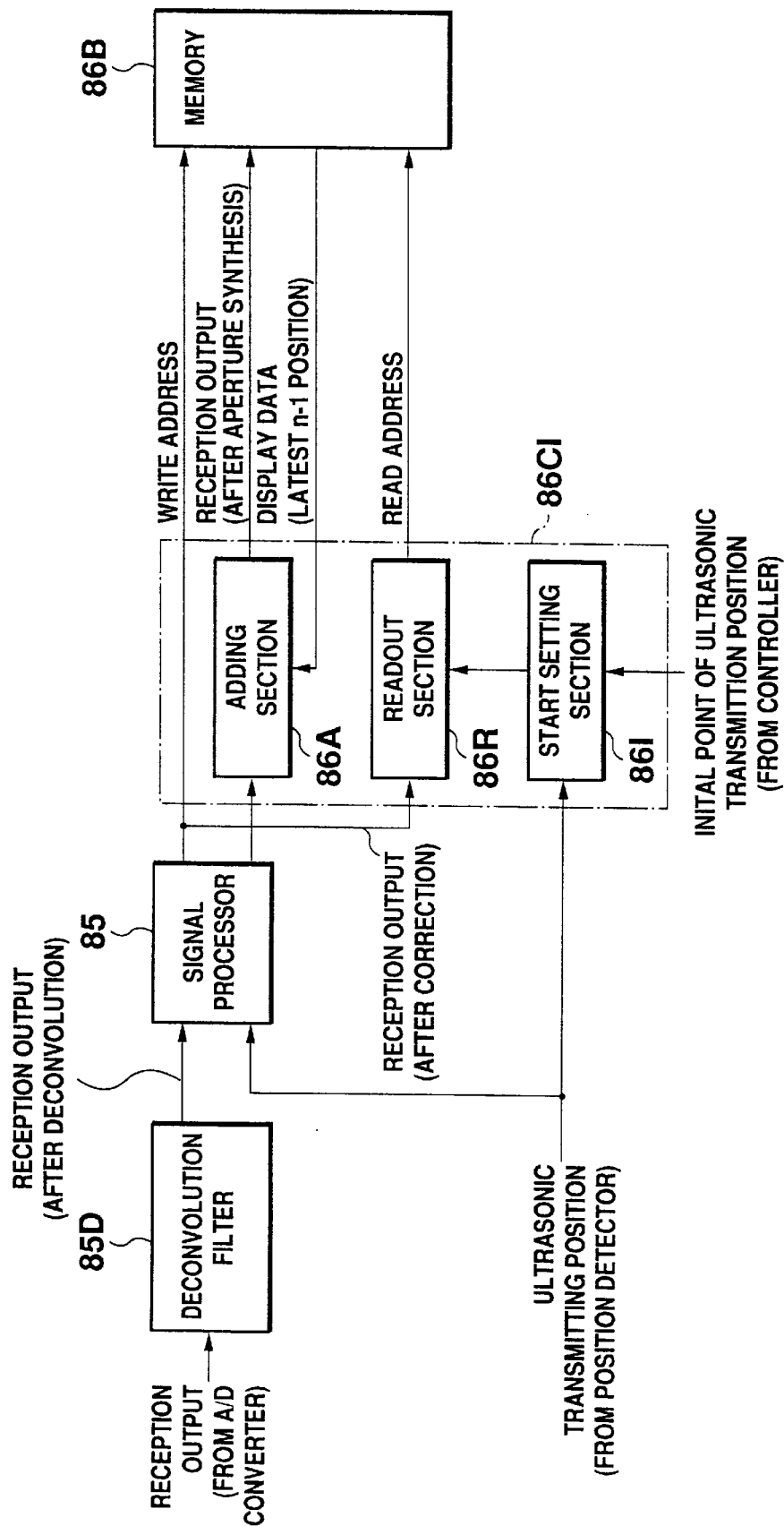
FIGS. 25, 26, 27, 28, 29, 30, 31, 32, 33 and 34 which show functions of display processors in a seventh, an eighth, a ninth, a tenth, an eleventh, a twelfth, a thirteenth, a fourteenth, a fifteenth, and a sixteenth embodiment of the present invention, respectively, with portions shown in FIG. 5 are omitted.
Figure 26:
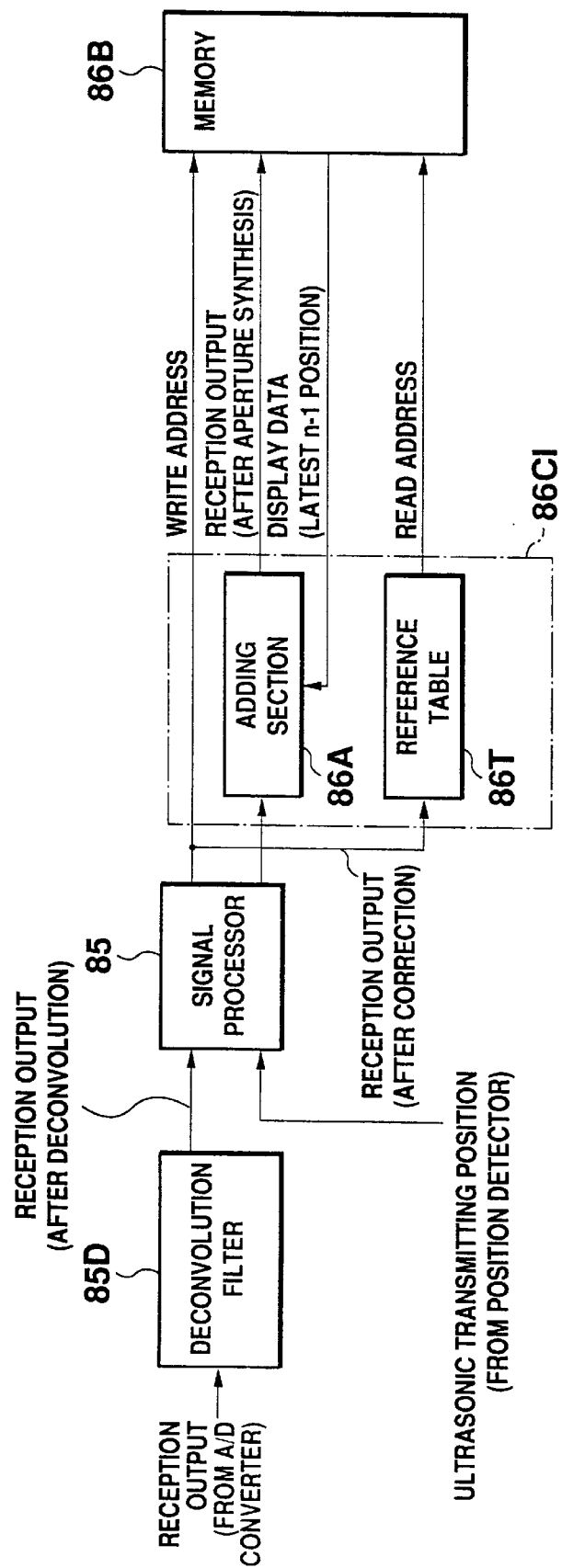
Figure 27:
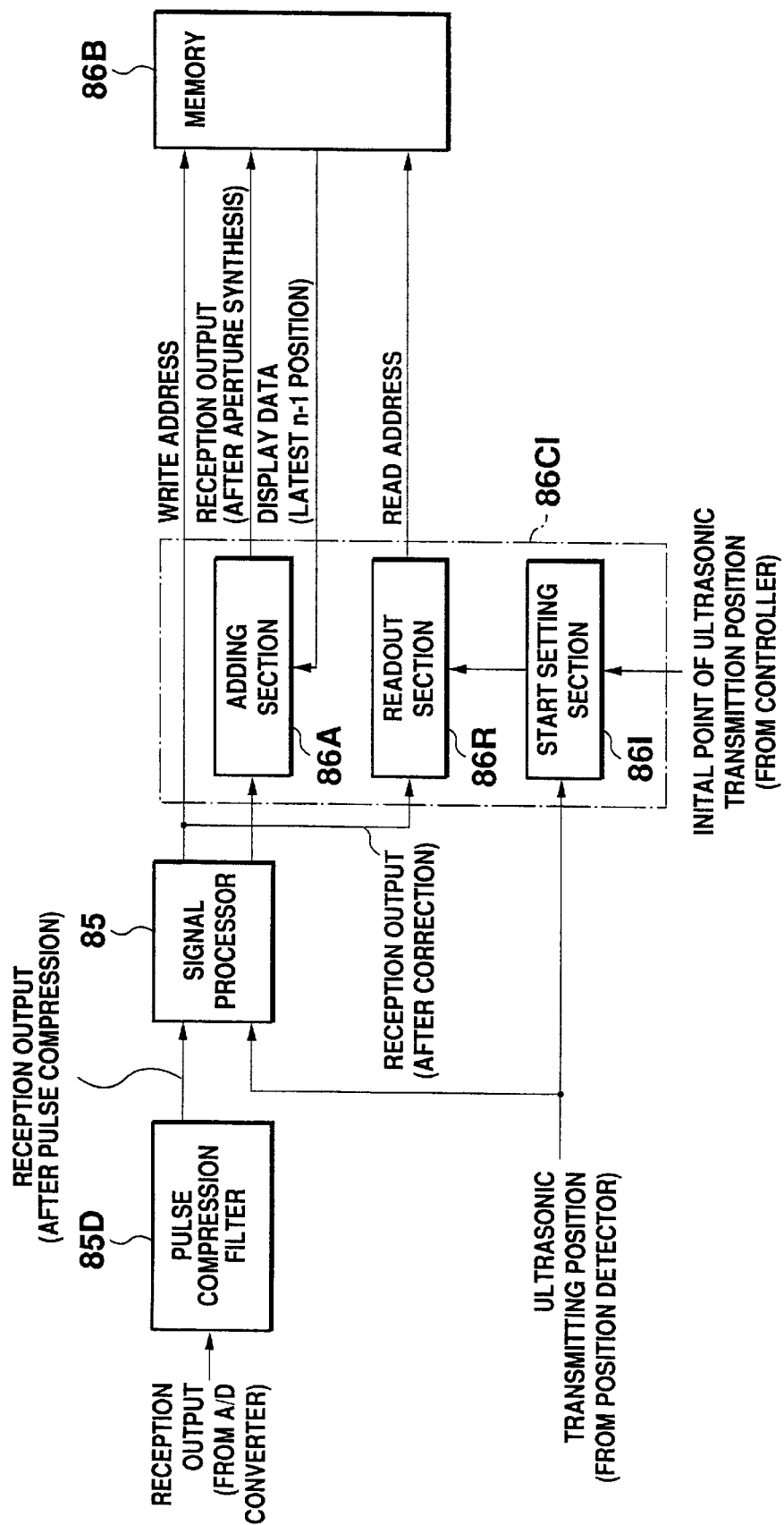
Figure 28:
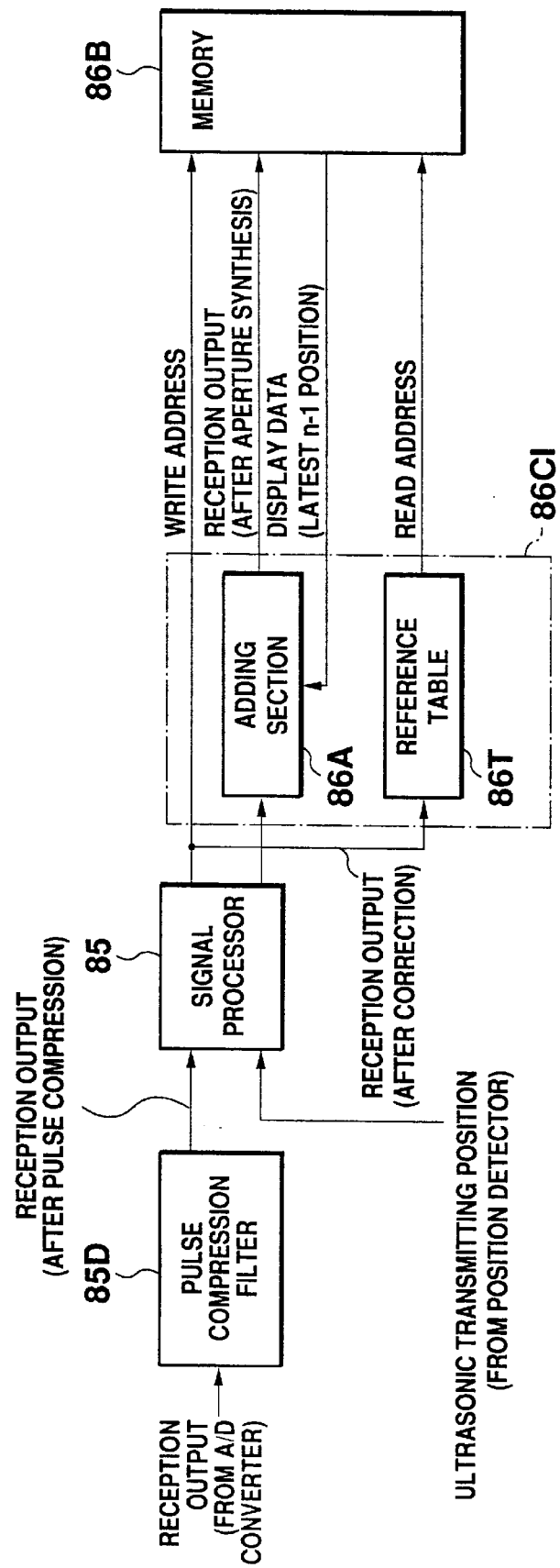
Figure 29:
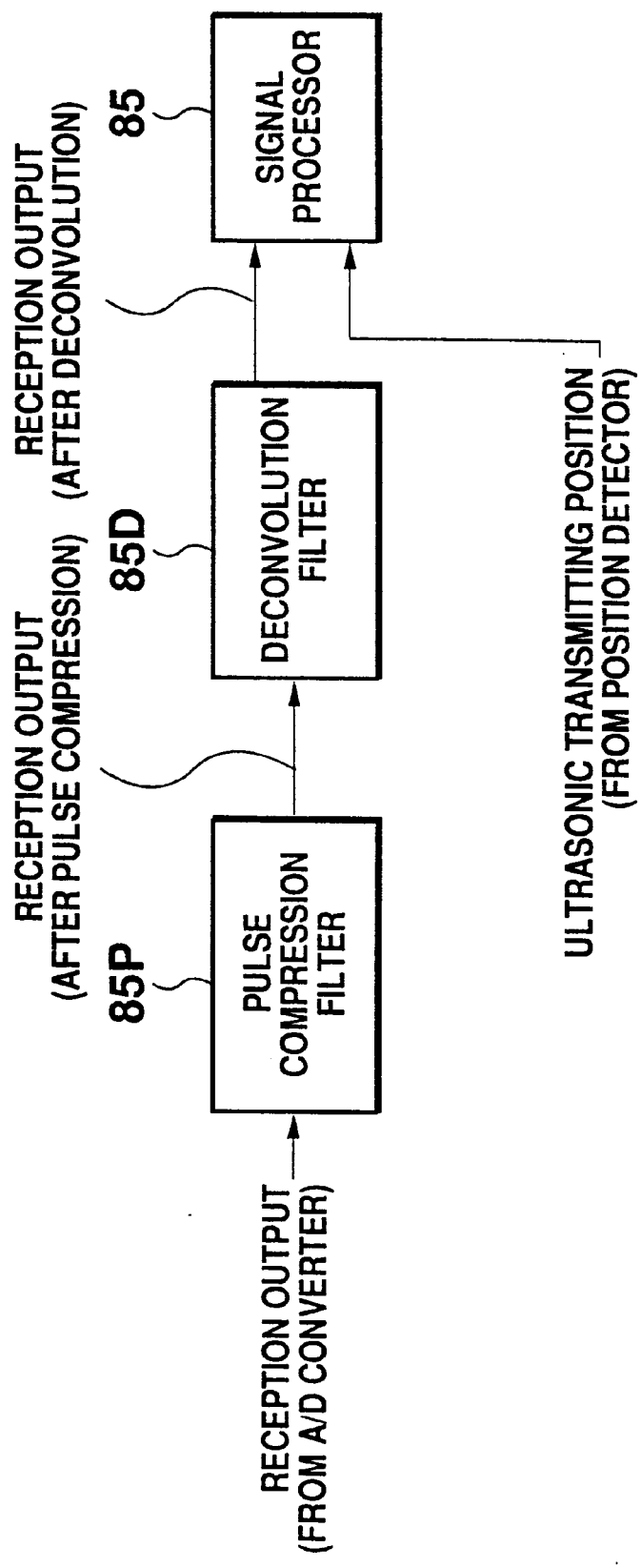
Figure 30:
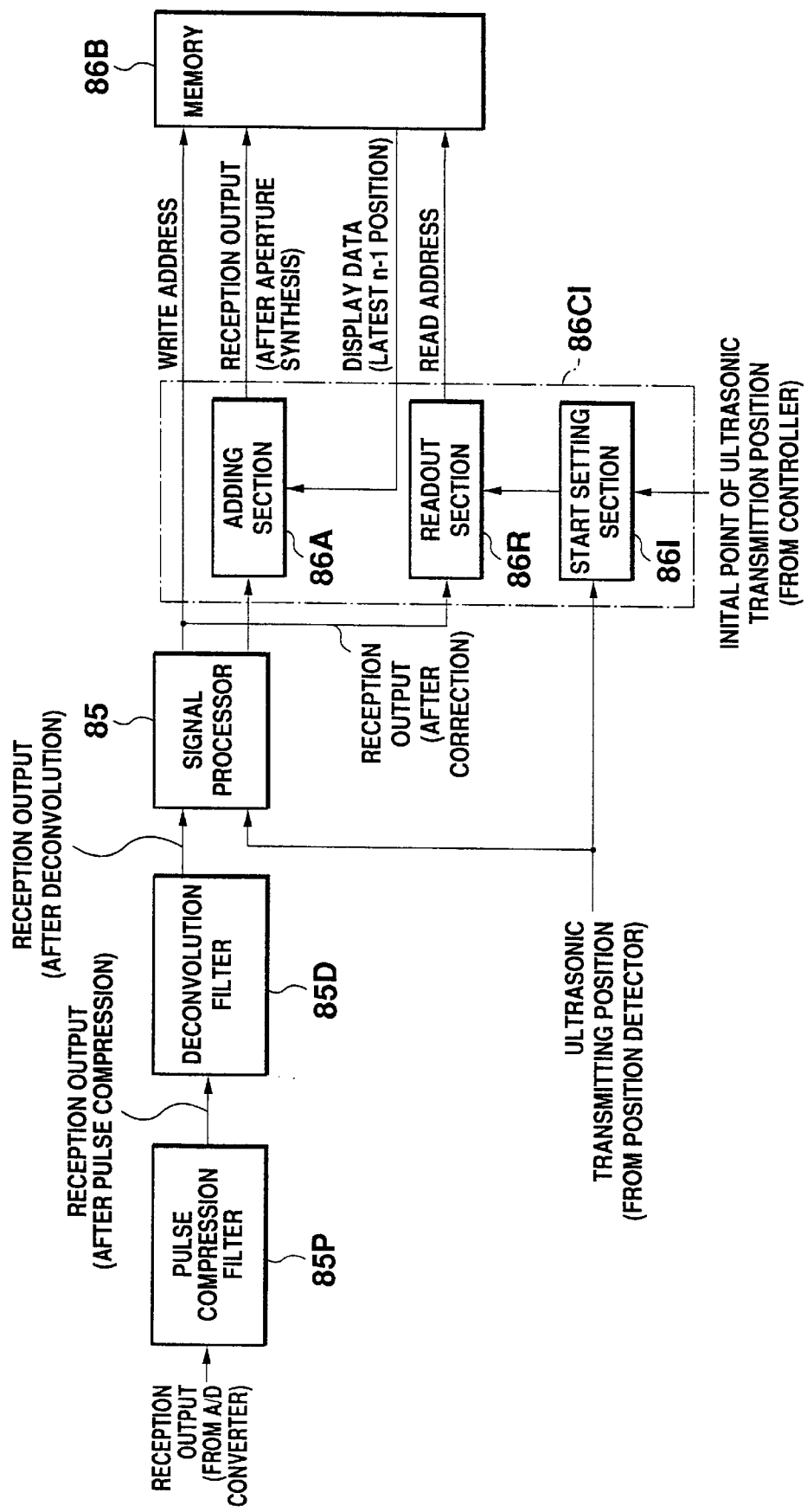
Figure 31:
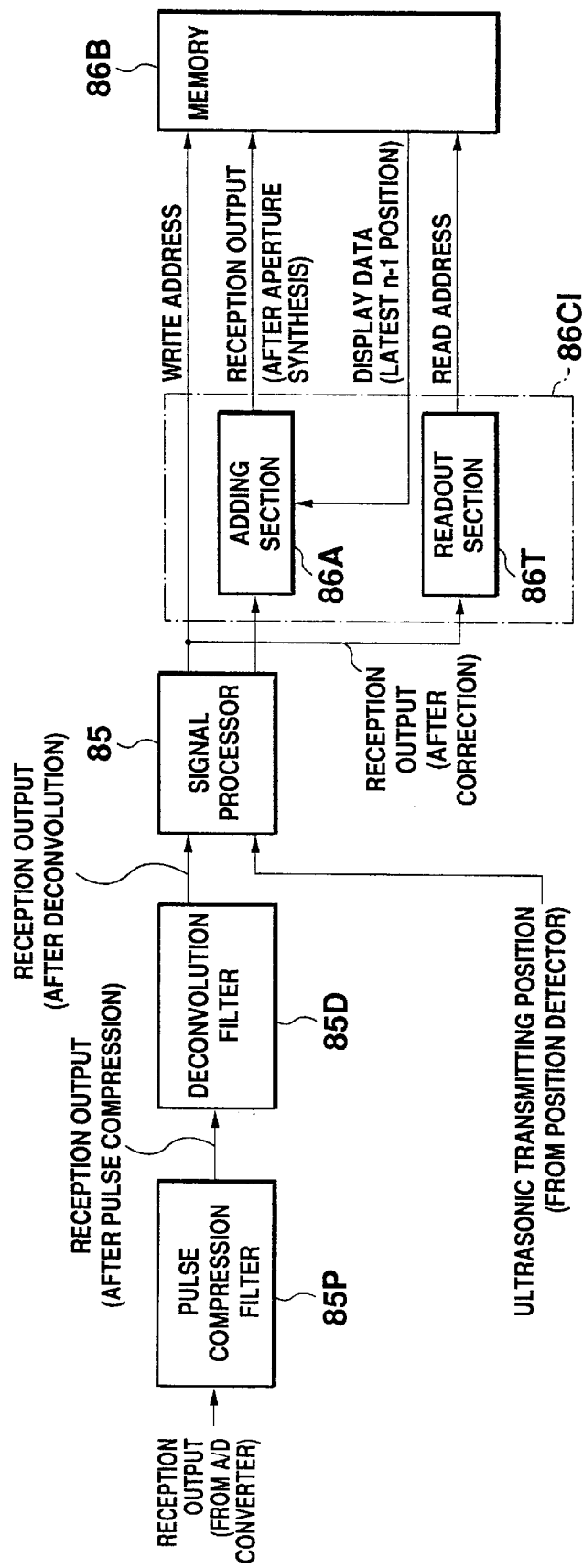

In ninth and tenth embodiments, which are shown in FIG. 27 and FIG. 28, respectively, the pulse compression filter 85P is provided in place of the deconvolution filter 85D which is used in the seventh and eighth embodiments, so that pulse compression and line aperture synthesis are carried out together. Further, in an eleventh embodiment shown in FIG. 29, both the pulse compression filter 85P and the deconvolution filter 85D are provided. In twelfth and thirteenth embodiments which are shown in FIG. 30 and FIG. 31, respectively, by adding the pulse compression filter 85P to the seventh and eighth embodiments which are shown in FIG. 25 and FIG. 26, respectively, three kinds of processes for reception outputs, such as line aperture synthesis, deconvolution and pulse compression, are carried out.

Each of the seventh to thirteenth embodiments can have an effect of the combined processes of reception outputs which are carried out in the respective embodiments. In FIGS. 25 to 31, members which are common with FIG. 5 are omitted.

FOURTEENTH, FIFTEENTH, AND SIXTEENTH EMBODIMENTS

Figure 32:
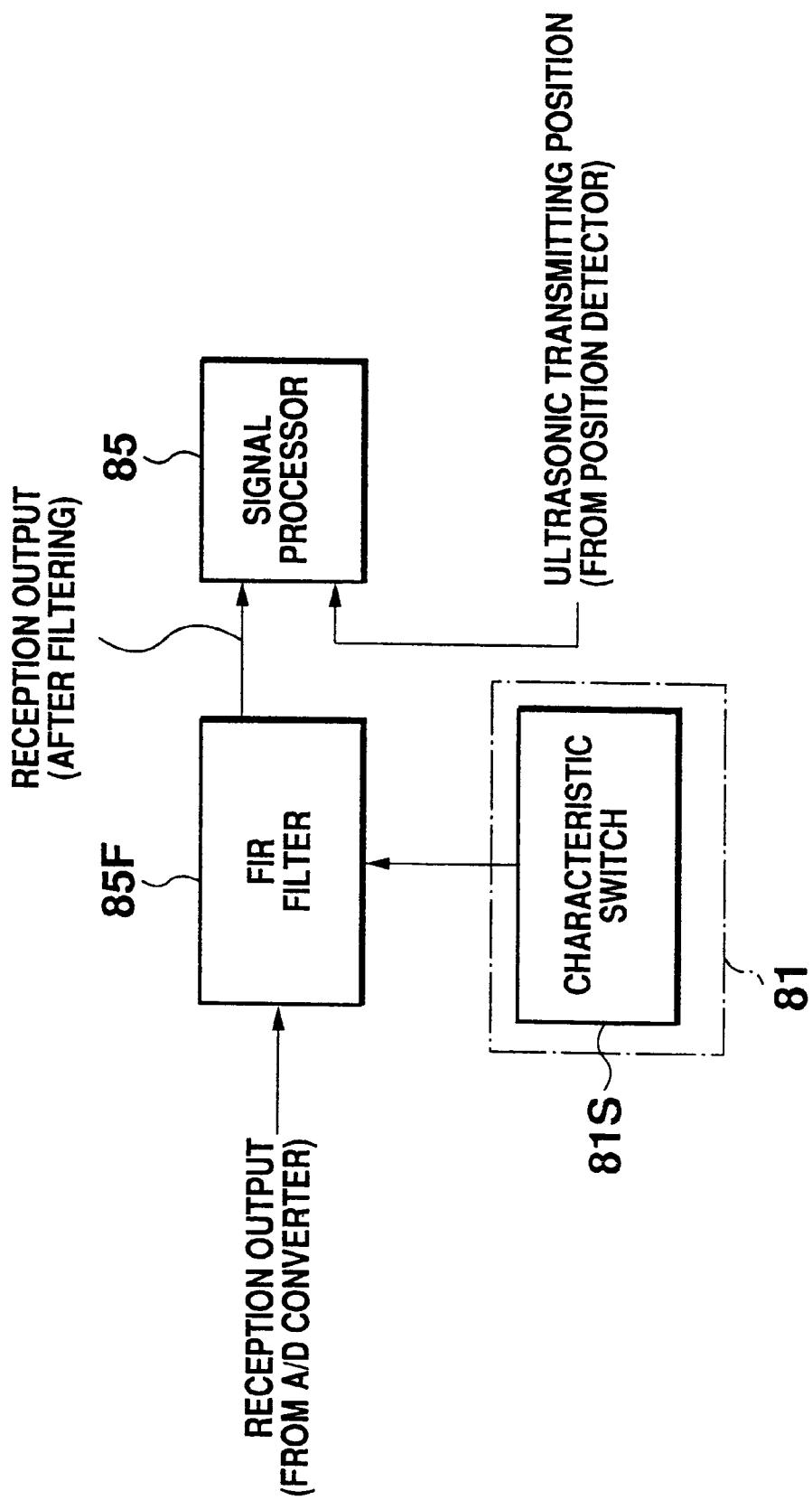

In FIG. 32, the function of a fourteenth embodiment of the present invention is shown. In this drawing, members which are common with these of FIG. 5 are omitted. This embodiment is characterized in that the pulse compression filter 85P and the deconvolution filter 85D in the eleventh embodiment shown in FIG. 29 are substituted by a finite impulse response (FIR) filter 85F which is a general purpose filter. More specifically, the controller 81 is provided with a characteristic switch 81S, and when a reception output from the A/D converter 84 is outputted to the signal processor 85, the FIR filter 85F filtrates the aforementioned reception output according to a the characteristic set by the characteristic switch 81S. The characteristic switch 81S switches the characteristic of the FIR filter 8SF, for example, in accordance with an instruction of a user. In other words, the characteristic switch 81S switches the characteristic of the FIR filter 85F in order for the FIR filter 85F to operate as the pulse compression filter 85P at an occasion, as the deconvolution filter 85D at another occasion, and as the combination of the pulse compression filter 85P and deconvolution filter 85D at the other occasion. By adopting such a constitution, in this embodiment, a constitution which is more simplified than that of the eleventh embodiment shown in FIG. 28 is realized, and application is possible wide.

Figure 33:
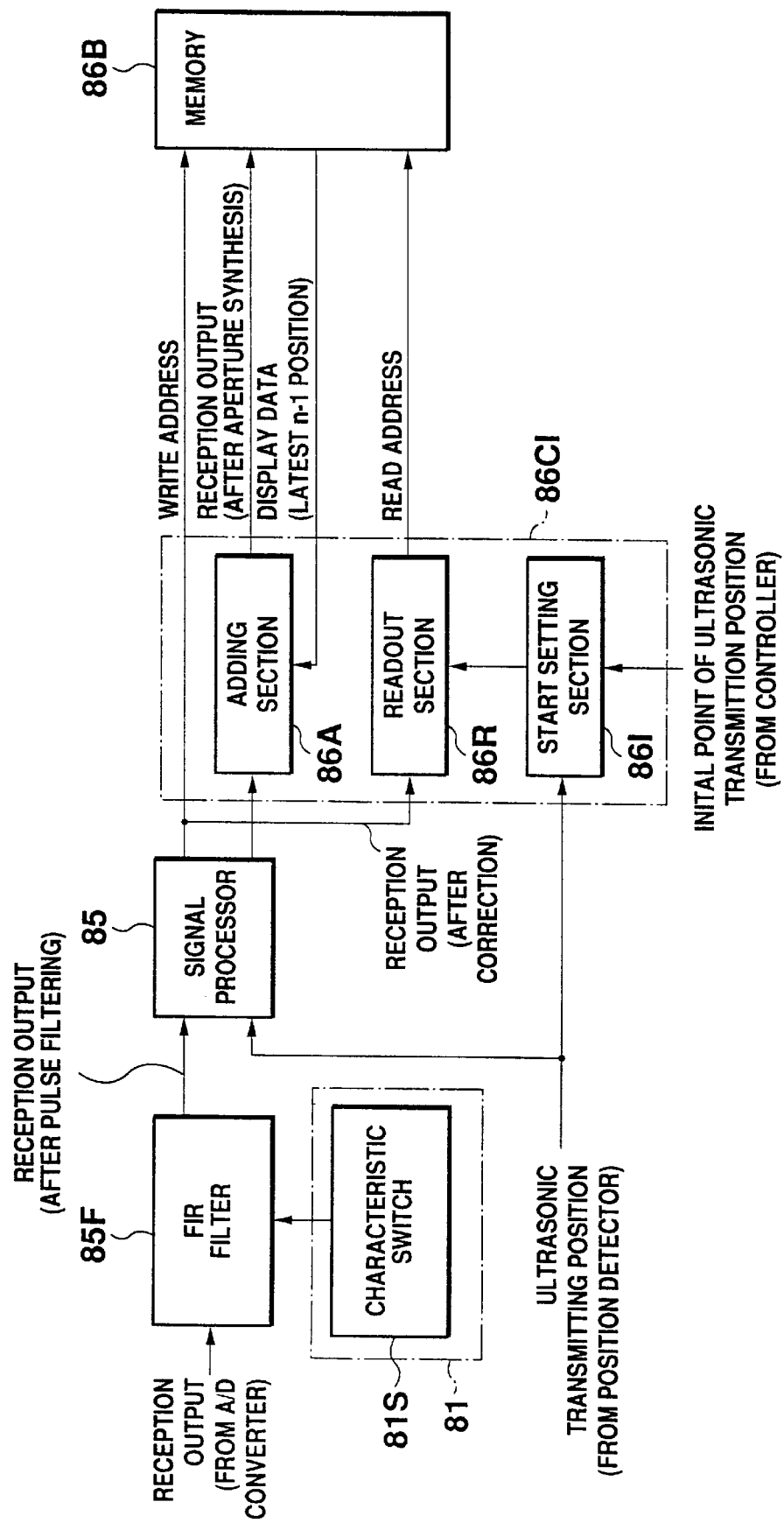
Figure 34:
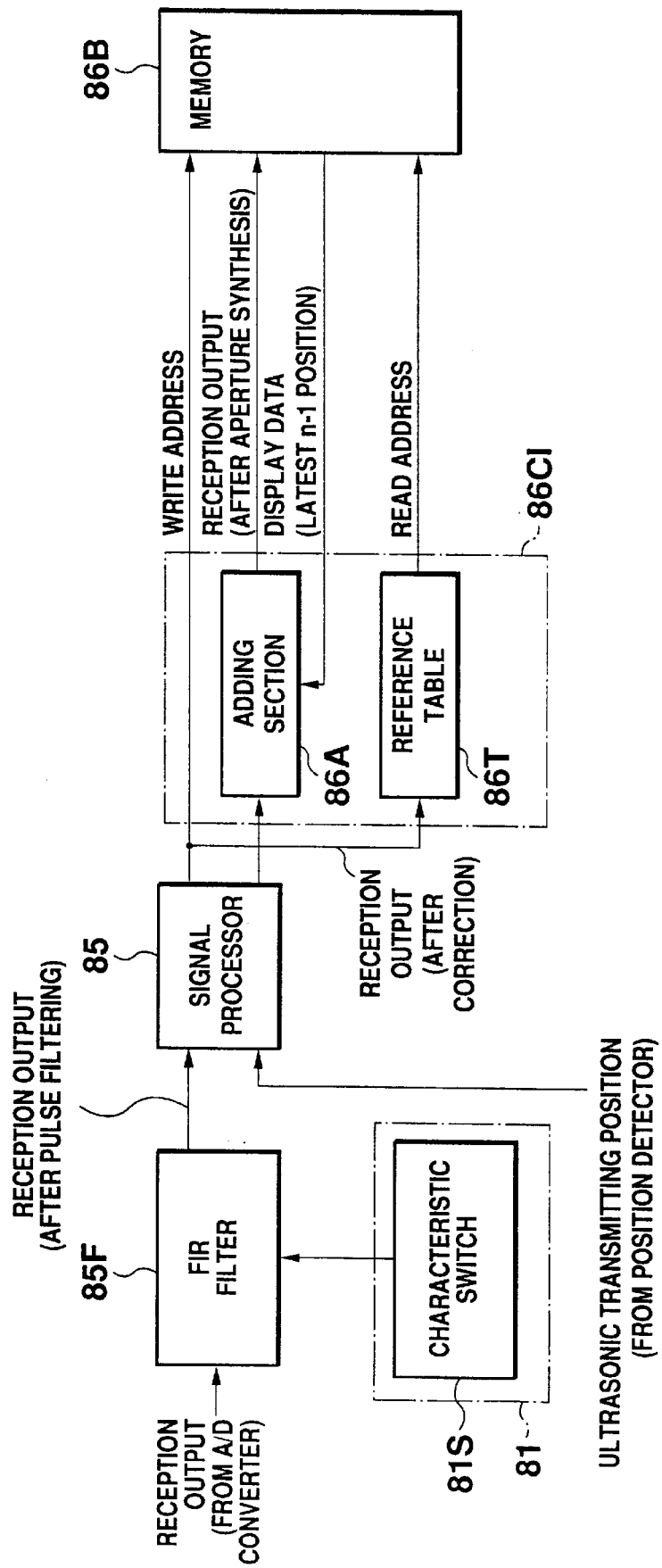

Fifteenth and sixteenth embodiments which are shown in FIG. 33 and FIG. 34, respectively, are embodiments in which modifications, similar to those applied to the eleventh embodiment so as to constitute the fourteenth embodiment, are applied to the twelfth and thirteenth embodiments which are shown in FIG. 30 and FIG. 31, respectively. Therefore, these fifteenth and sixteenth embodiments can have the effect of the fourteenth embodiment as well as the effects of the twelfth and thirteenth embodiments. In FIGS. 33 and 34, the members which are common with FIG. 5 are omitted.

A SEVENTEENTH EMBODIMENT

Figure 35:
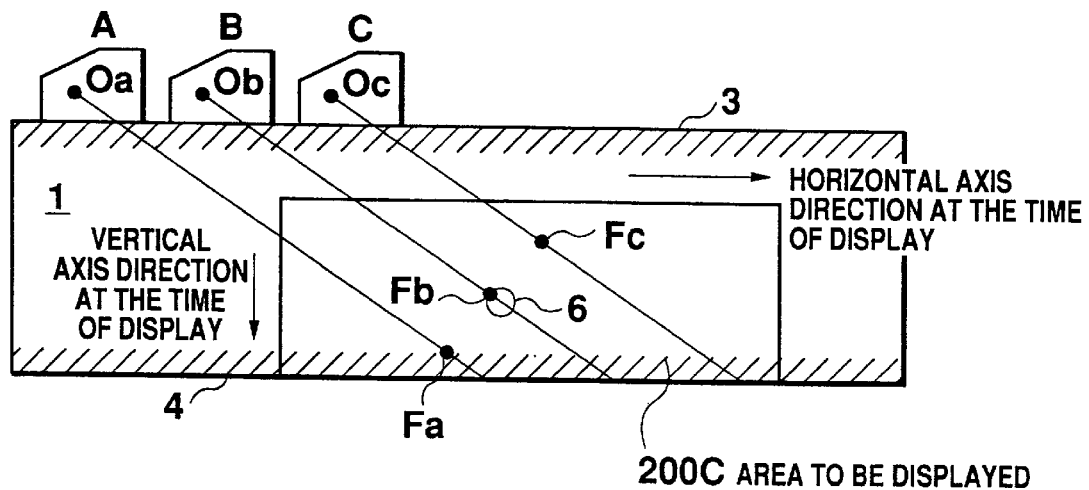
FIGS. 35 and 36 are conceptual drawings which show time axis inclination and the effect thereof in a seventeenth embodiment of the present invention, respectively.
Figure 36:
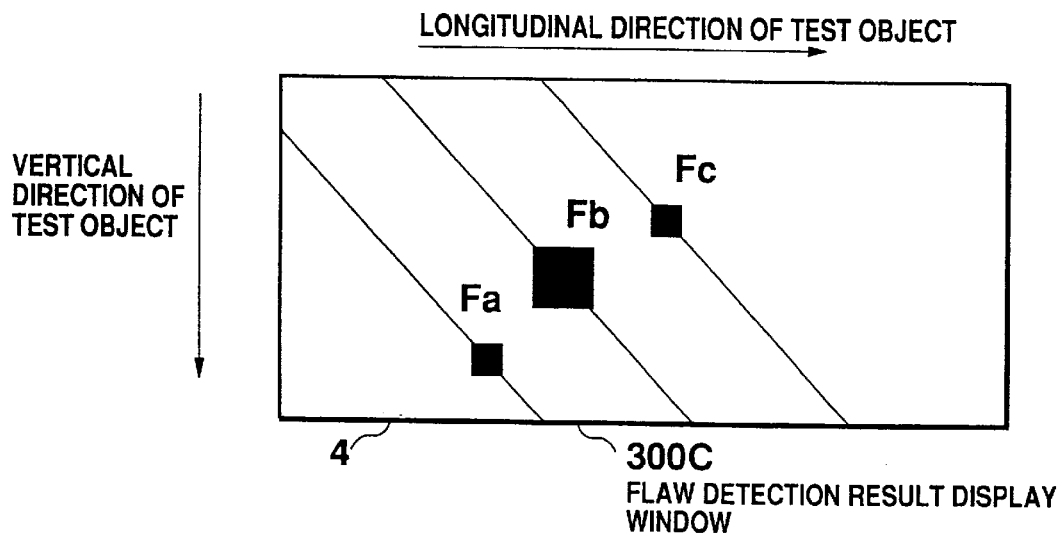

The first to sixteenth embodiments described above are constituted presupposing the presence of the rectangular area 200A as shown in FIG. 11, in which on side of the area is parallel to an ultrasonic transmitting direction and the other side is orthogonal to the ultrasonic transmitting direction. However, when the present invention is brought into practice, an area to be displayed should not be limited to the area 200A. A seventeenth embodiment of the present invention uses an area to be displayed 200C whose one side is parallel to and the other side is orthogonal to the surface 3 of the test object 1 as shown in FIG. 35, whereby the modified B scope as shown in FIG. 36 is provided. By adopting such a display mode, this embodiment provides a user friendly device.

Figure 37:
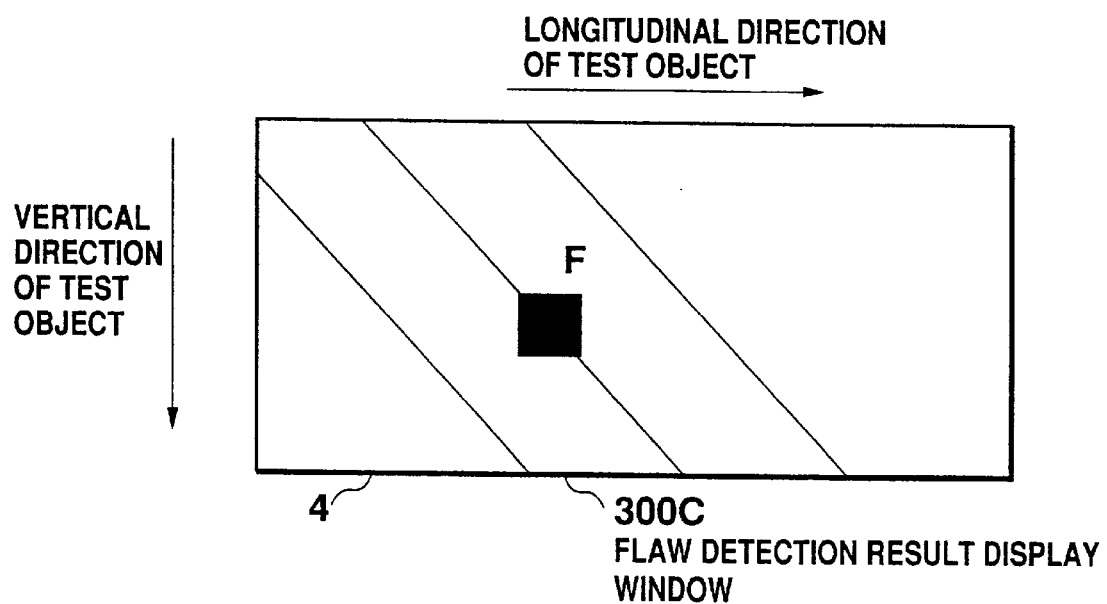
FIG. 37 shows example display windows of the seventeenth embodiment of the present invention.
Figure 38:
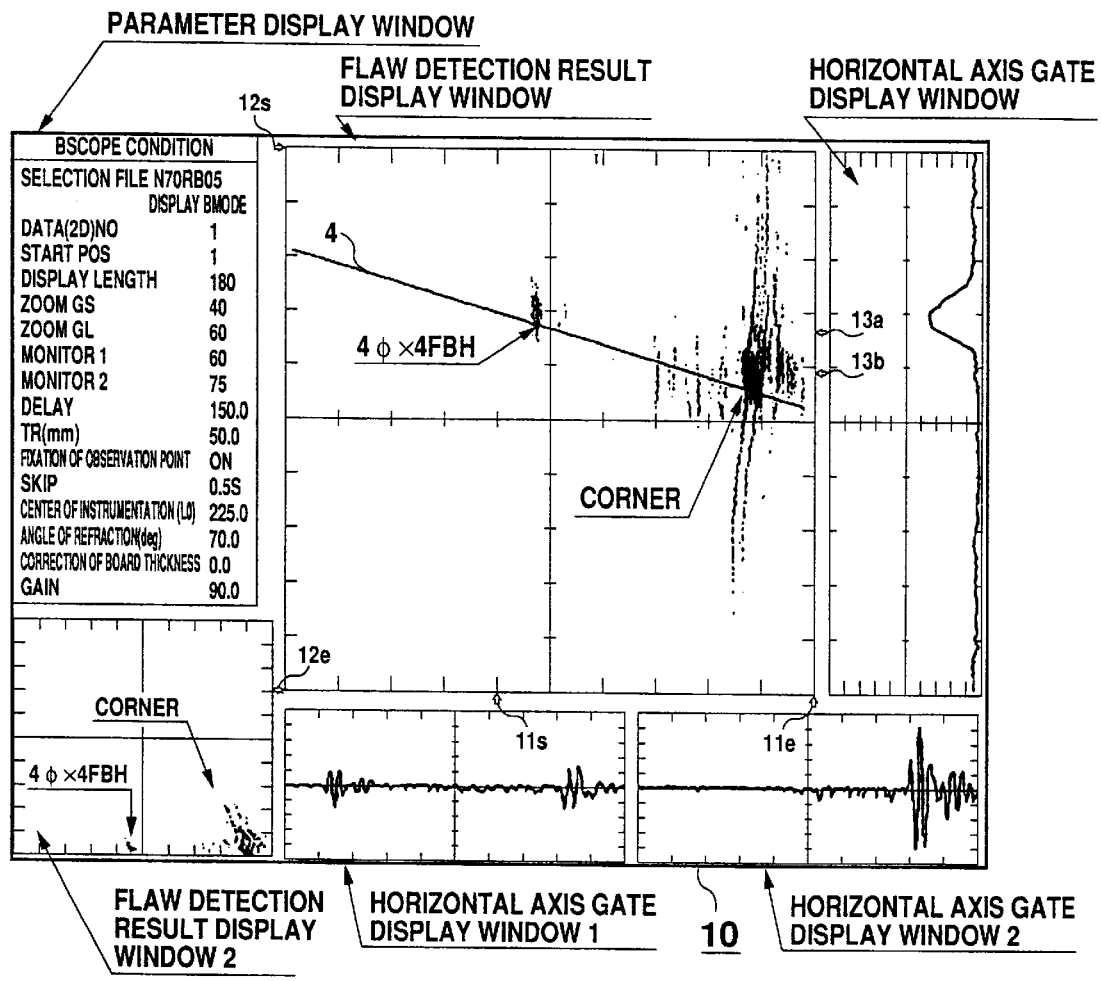
FIG. 38 is a hard copy of a screen which shows a modified B scope formed according to the seventeenth embodiment using the sample of FIG. 13.
Figure 39:
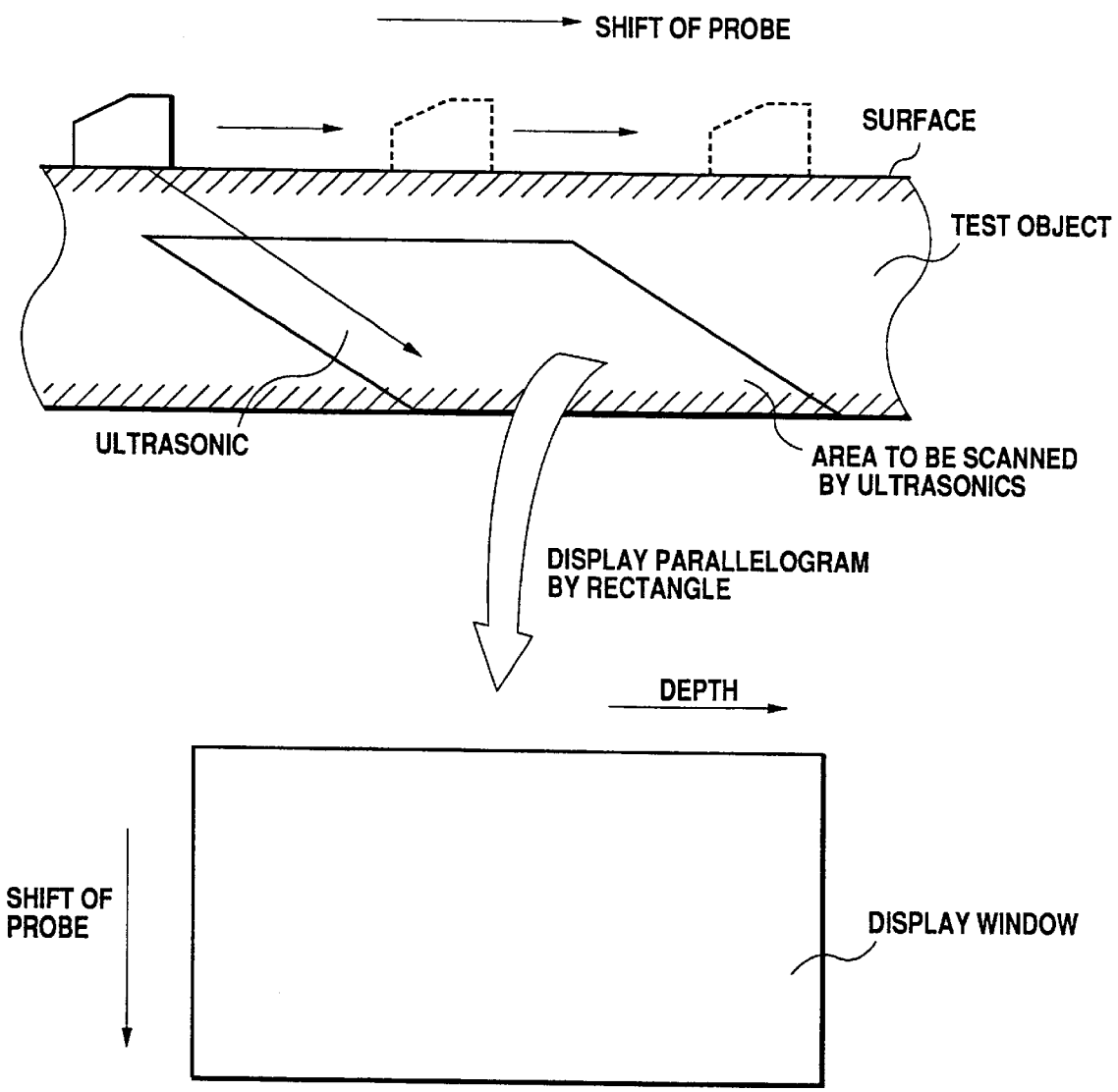
FIG. 39 is a conceptual drawing for the explanation of the conventional problems.

FIGS. 37 and 38 show the modified B scope in this embodiment when the sample shown in FIG. 13 is used as the test object. In FIG. 38, the composition of screen shown in FIG. 14 is utilized, and also a display by ondogram is performed in a first flaw detection result display window as shown in the second embodiment, while a display by area is performed in a first flaw detection result display window as shown in the second embodiment, respectively. As it is obvious from the drawing, in this embodiment, the difference in their nature between corners and holes which are the discontinuity 6 is clearly displayed as it is given in the description of the second embodiment, and also the bearing resolution and signal-to-noise ratio are improved as it is given in the description of this embodiment. Further, by performing a line aperture synthesis, it is possible to realize enhanced and focussed echo display, such as shown in FIGS. 37 and 38.

In order to realize the modified B scope using the area to be displayed 200C and the flaw detection result display window 300C which are shown in FIG. 35 and FIG. 36, respectively, it is necessary for the signal processor 85 to perform even a rotation of coordinates i.e. inclining time axes, in addition to the time axis origin shifting. Also, it should be noted that the area to be displayed 200C belongs to a plane which is or will be scanned by ultrasonics, like the area to be displayed 200A.

While there have been described what are at present considered to be preferred embodiments of the invention, it will be understood that various modifications maybe made thereto, and it is intended that the appended claims cover all such modifications as fall within the true spirit and scope of the invention.

What is claimed is:

1. An ultrasonic transceiver comprising:
an angle ultrasonic probe arranged on a surface of a test object to transmit to and receive from an interior of the test object at an ultrasonic transmitting direction inclined with respect to the surface of the test object;
a scanning mechanism causing a shifting of an ultrasonic transmitting position by the angle ultrasonic probe along the surface of the test object;
a display device displaying, on the basis of received output of the angle ultrasonic probe, an image showing the presence or nature of a discontinuity in the test object; and
a signal processor performing a signal processing on the received output and supplying a processed received output to the display device;
wherein the signal processing shifts an origin position of a time axis as the ultrasonic transmitting position shifts to arrange on a line parallel to a scanning direction axis a plurality of images obtained with a same ultrasonic transmission time, the time axis being an axis representing a time elapse from ultrasonic incidence into the test object and the scanning direction axis being an axis representing a position along a shifting direction of the angle ultrasonic probe.

2. The ultrasonic transceiver according to claim 1, further comprising a position detector detecting the ultrasonic transmitting position, wherein the signal processing determines a shift width of the origin position of the time axis on the basis of the ultrasonic transmitting position and angle information indicative of the ultrasonic transmitting direction and shifts the origin position of the time axis in accordance with the shift width.

3. The ultrasonic transceiver according to claim 2, further comprising a memory storing the processed received output to supply the processed received output to the display device, wherein the signal processing modifies a memory write address in compliance with the shift width.

4. The ultrasonic transceiver according to claim 2, further comprising a controller supplying angle information to the signal processor in response to a user input.

5. The ultrasonic transceiver according to claim 1, the image being selected from a group consisting of: a first image having an area indicative of signal strength of an echo from the discontinuity; a second image having a color indicative of signal strength of the echo; and a third image indicative of a signal waveform of the received output.

6. The ultrasonic transceiver according to claim 5, further comprising a controller which instructs, to the signal processor, which one of the first, second and third images should be displayed.

7. The ultrasonic transceiver according to claim 1, further comprising an aperture synthesizer performing an aperture synthesis on the received output or the processed received output to be supplied to the display device, the aperture synthesis being a process for apparently enhancing an aperture of the angle ultrasonic probe by combining the received output or the processed received output to a previously-obtained received output or a processed received output.

8. The ultrasonic transceiver according to claim 7, in which the aperture synthesizer includes a table correlating the ultrasonic transmitting position, a distance from the ultrasonic transmitting position, and a position in the interior of the test object, and in which the aperture synthesizer performs the aperture synthesis is by referring the table.

9. The ultrasonic transceiver according to claim 1, further comprising a deconvolution filter performing a deconvolution on the received output or the processed received output to be supplied to the display device, the deconvolution being a process for convoluting characteristics of the received output or the processed received output and characteristics which are reciprocal to characteristics relating to transmitting and receiving operation of ultrasonics and are included in the characteristics of the received output.

10. The ultrasonic transceiver according to claim 1, further comprising a transmitter transmitting from the angle ultrasonic probe ultrasonics with modulated phase and a pulse compression filter performing a pulse compression on the received output or the processed received output to be supplied to the display device, the pulse compression being a process for increasing an energy density in the received output by utilizing correlation between a phase modulation signal previously utilized to modulate transmitting ultrasonics and the received output.

11. The ultrasonic transceiver according to claim 9, further comprising a transmitter transmitting from the angle ultrasonic probe ultrasonics with modulated phase and a pulse compression filter performing a pulse compression on the received output or the processed received output to be supplied to the display device; the pulse compression being a process for increasing an energy density in the received output by utilizing a correlation between a phase modulation signal previously utilized to modulate transmitting ultrasonics and the received output.

12. The ultrasonic transceiver according to claim 11, further comprising a controller which instructs a process selected from a group consisting of deconvolution, pulse compression, or a combination thereof; and a characteristic switching filter which operates as either the deconvolution filter, the pulse compression filter, or a combination filter in response to an instruction from the controller, the combination filter having characteristics being equivalent to a combination of the deconvolution filter and the pulse compression filter.

13. The ultrasonic transceiver according to claim 1, further comprising a display processor controlling an arrangement of a plurality of display windows on a screen of the display device, at least one of the plurality of the display windows being used as a window for displaying the image indicative of the processed received output.

14. The ultrasonic transceiver according to claim 13, in which at least two of the plurality of display windows are used as windows for displaying mutually different images each indicative of the processed received output, the mutually different images to be compared being selected from a group consisting of images showing a same processed received output in mutually different image format; images showing mutually different processed received outputs obtained by performing mutually different type of processes on a same received output; and images showing mutually different processed received outputs each obtained from different test objects.

15. The ultrasonic transceiver according to claim 13, in which at least one of the plurality of display windows being used as a gate inside window for displaying an image which is an extracted part of an image obtained from the processed received output; or for displaying a modified image obtained by modifying the extracted part, the extracted part being designated by a user input, through the display processor, using a time axis gate marker for designating an area on the time axis.

16. The ultrasonic transceiver according to claim 13, in which at least one of the plurality of display windows are used as a gate inside window for displaying an image which is an extracted part of the image obtained from the processed received output or for displaying a modified image obtained by modifying the extracted part, the extracted part being designated by a user input, through the display processor, using a scanning direction axis gate marker for designating an area on the scanning direction axis.

17. The ultrasonic transceiver according to claim 13, in which at least one of the plurality of display windows is used as a gate inside window for displaying an image which is an extracted part of the image obtained from the processed received output or for displaying a modified image obtained by modifying an extracted part designated by a user input, through the display processor, using a probe position designating marker for designating one ultrasonic transmitting position and a time axis gate marker for designating an area on the time axis.

18. The ultrasonic transceiver according to claim 13, in which at least one of the plurality of display windows being used as a parameter display window for displaying a condition which is manually set by a user or automatically set by the ultrasonic transceiver, the condition being in connection with at least one of transmittance of ultrasonics, reception of ultrasonics, or display of the processed received output.

19. The ultrasonic transceiver according to claim 1, implemented as an ultrasonic flaw detector for searching a discontinuity in the test object without causing a damage to the test object, the test object being a board material, a tubular material or a welded workpiece, and in which the discontinuity is a foreign contaminant, an aperture, or a structural defect in the test object.

20. An ultrasonic transceiver comprising:
a plurality of angle ultrasonic probes arranged along a line parallel to a surface of a test object for transmitting ultrasonics to and receiving ultrasonics from an interior of the test object, ultrasonic transmitting directions from each of the plurality of angle ultrasonic probes being inclined with respect to the surface of the test object;

a switch circuit selectively and sequentially operating the plurality of angle ultrasonic probes along the line;

a display device displaying, on the basis of received output of the plurality of angle ultrasonic probes, an image showing the presence or nature of a discontinuity in the test object; and a signal processor performing a signal processing on the received output and supplying a processed received output to the display device;

wherein the signal processing shifts an origin position of a time axis as an operating probe switches, to arrange on a line parallel to a scanning direction axis a plurality of images obtained with a same ultrasonic transmission time, the time axis being an axis representing a time elapse from ultrasonic incidence into the test object and the scanning direction axis being an axis representing a sequential switching direction by the switch circuit.

21. A signal processor used in an ultrasonic transceiver, in which the ultrasonic transceiver transmits ultrasonics into a test object and receives an echo from an interior of the test object while shifting an ultrasonic transmitting position along a surface of the test object and maintaining an inclined ultrasonic transmitting direction, and displays on a screen an image indicative of presence or nature of a discontinuity in the test object on the basis of a result of reception, the signal processor further comprising:

a position detector detecting the ultrasonic transmitting position; and a display processor performing a process for shifting an origin position of a time axis as the ultrasonic transmitting position shifts by modifying the result of reception on the basis of a detected ultrasonic transmitting position and an information indicative of the ultrasonic transmitting direction, so as to arrange on a scanning direction axis a plurality of images obtained with a same ultrasonic transmission time; and wherein the time axis represents a time elapse from ultrasonic incidence into the test object and the scanning direction axis represents a shifting direction of the ultrasonic transmitting position.

* * * * *